1

(12) United States Patent
Hölscher et al.

(10) Patent No.: US 6,841,550 B1
(45) Date of Patent: Jan. 11, 2005

(54) BENZOXAZINE AND BENZOTHIAZINE DERIVATIVES AND THEIR USE IN MEDICINES

(75) Inventors: Peter Hölscher, Berlin (DE); Hartmut Rehwinkel, Berlin (DE); Stefan Jaroch, Berlin (DE); Detlev Sülzle, Berlin (DE); Margrit Hillmann, Berlin (DE); Gerardine Anne Burton, Berlin (DE); Fiona Mcdougall McDonald, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/787,396

(22) PCT Filed: Sep. 16, 1999

(86) PCT No.: PCT/EP99/07089

§ 371 (c)(1),
(2), (4) Date: Mar. 19, 2001

(87) PCT Pub. No.: WO00/17173

PCT Pub. Date: Mar. 30, 2000

(30) Foreign Application Priority Data

Sep. 18, 1998 (DE) ...................................... 198 44 291.2

(51) Int. Cl.[7] ..................... A61K 31/538; C07D 265/36

(52) U.S. Cl. ............................... 514/229.8; 514/230.5; 544/101; 544/105

(58) Field of Search ................................ 544/105, 101; 514/229.8, 230.5

(56) References Cited

U.S. PATENT DOCUMENTS 6,365,736 B1   4/2002   Holscher et al. ............ 544/105

FOREIGN PATENT DOCUMENTS

| DE | 25 09 155 | 9/1976 |
| WO | 97/45419 | 12/1997 |
| WO | 98/50372 | 11/1998 |
| WO | 99/12915 | 3/1999 |

OTHER PUBLICATIONS

Gauthier et al., Chem. Abstracts, 28–Heterocycles, vol. 111, 1989, p. 603–604.
Bockert et al., Chem. Abstracts, 28–Heterocycles, vol. 115, 1991, p. 1019.
Nakame et al., Chem. Abstracts, vol. 122, 1995, p. 54.

*Primary Examiner*—Richard L. Raymond
(74) *Attorney, Agent, or Firm*—Millen, White, Zelano & Branigan, P.C.

(57) ABSTRACT

The invention relates to compounds of formula (I) and their tautomeric and isomeric forms and salts, as well as to a method for producing said compounds and their use in medicines.

17 Claims, No Drawings

BENZOXAZINE AND BENZOTHIAZINE DERIVATIVES AND THEIR USE IN MEDICINES

The invention relates to benzoxazine and benzothiazine derivatives, the process for their production and their use in pharmaceutical agents.

In human cells, there exist at least 3 forms of nitrogen monoxide synthases, which convert arginine into nitrogen monoxide (NO) and citrulline. Two constitutive NO-synthases (NOS) were identified that are present as calcium/calmodulin-dependent enzymes in the brain (ncNOS or NOS 1) or in the endothelium (ecNOS or NOS 3) Another isoform is the inducible NOS (iNOS or NOS 2), which is a virtually $Ca^{++}$-independent enzyme and is induced after activation of different cells by endotoxin or other substances.

NOS-inhibitors and especially selective inhibitors of NOS 1, NOS 2 or NOS 3 are therefore suitable for treatment of different diseases, which are induced or aggravated by pathological concentrations of NO in cells. A number of reviews provide information on the action and inhibitors of NO-synthases. Mentioned are, for example: Drugs 1998, 1, 321 or Current Pharmac. Design 1997, 3, 447.

As NOS-inhibitors, different compounds are known. For example, arginine derivatives, aminopyridines, cyclic amidine derivatives, phenylimidazoles, etc. are described. It is not known from any publication that 1,4-benzoxazines and 1,4-benzothiazines inhibit nitrogen monoxide synthases in a potent and selective manner.

It has now been found that the heterocycles that are substituted according to the invention, compared to known compounds, can be used especially advantageously as pharmaceutical agents.

The invention relates to the compounds of formula I, their tautomeric and isomeric forms and salts

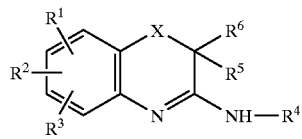

(I)

in which
X is O, $SO_m$ or Se,
$R^1$ is $-(CHR^9)_n-NR^7-A-NR^8-B$,
$R^2$ is hydrogen or
$R^1$ and $R^2$ together with two adjacent carbon atoms form a 5-, 6-, 7- or 8-membered ring, which is monocyclic or bicyclic, saturated or unsaturated and in which 1 or 2 $CH_2$ groups can be replaced by oxygen or carbonyl, and which is substituted with $(CHR^9)_r-NR^7-A-NR^8-B$, and can be substituted with $C_{1-4}$ alkyl,
$R^3$ means hydrogen, halogen, $NO_2$, cyano, $CF_3$, $-OCF_3$, $-S-R^9$, $-O-R^9$, $C_{3-7}$ cycloalkyl, $-NR^9-C(=NR^{10})-R^{11}$, $-NH-CS-NR^{12}R^{13}$, $NH-CO-NR^{12}R^{13}$, $-SO_2NR^{12}R^{13}$, $-CO-NR^{12}R^{13}$, $-CO-R^{14}$, $NR^{15}R^{16}$, $C_{6-10}$ aryl, which optionally is substituted with halogen, cyano, $C_{1-4}$ alkyl, $-S-R^9$, or $-O-R^9$,
5- or 6-membered heteroaryl with 1 to 4 oxygen, sulfur or nitrogen atoms,
$C_{1-6}$ alkyl, which optionally is substituted with halogen, $-OR^9$, $-SR^9$, $-NR^{12}R^{13}$, $=NR^{12}$, $=NOC_{1-6}$ alkyl, $=N-NH$ aryl, phenyl, $C_{3-7}$ cycloalkyl or 5- or 6-membered heteroaryl,
$C_{2-6}$ alkenyl, which optionally is substituted with halogen, $CONH_2$, $C\equiv N$ or phenyl,
$C_{2-6}$ alkinyl, which optionally is substituted with halogen, $CONH_2$, $C\equiv N$ or phenyl,
$R^4$ means hydrogen or acyl,
$R^5$ and $R^6$, independently of one another, mean hydrogen, $C_{3-7}$ cycloalkyl, phenyl, $C_{1-6}$ alkyl, $C_{2-6}$ alkenyl or $C_{2-6}$ alkynyl radicals; which can be substituted in each case with halogen, OH, $O-C_{1-6}$ alkyl, SH, $S-C_{1-6}$ alkyl, $NR^{15}R^{16}$, 5- or 6-membered heteroaryl with 1–3N, O or S atoms, phenyl or $C_{3-7}$ cycloalkyl;
$R^7$ means hydrogen, $C_{1-6}$ alkyl, which can be substituted with phenyl, $COOC_{1-6}$ alkyl or $CO-C_{1-6}$ alkyl,
$R^8$ means hydrogen, $C_{1-6}$ alkyl, which can be substituted with phenyl, $COOC_{1-6}$ alkyl or $COC_{1-6}$ alkyl,
A means straight-chain or branched $C_{1-6}$ alkylene, straight-chain or branched $C_6$ alkenylene or $-(CH_2)_p-Q-(CH_2)_q-$,
B means hydrogen or $-(CH_2)_p-U$,
Q means $C_{3-7}$ cycloalkyl, indanyl, 5-, 6- or 7-membered saturated heterocycloalkyl with 1–2 N, O or S atoms, $C_6-C_{10}$ aryl or 5- or 6-membered heteroaryl with 1–3 N, O or S atoms, which can be anellated with benzene,
U means hydrogen, $C_{1-6}$ alkyl optionally substituted with halogen, $C_{3-7}$ cycloalkyl, indanyl, $C_{7-10}$ bicycloalkyl, $C_{6-10}$ aryl or 5- or 6-membered heteroaryl with 1–3 N, O or S atoms, which can be anellated with benzene, whereby the aryl and heteroaryl radical can be substituted with halogen, $C_{1-4}$ alkyl, $C_{1-4}$ alkoxy, $CF_3$, $NO_2$, $NH_2$, $N(C_{1-4}$ alkyl$)_2$, cyano, $CONH_2$, $-O-CH_2-O-$, $-O-(CH_2)_2-O-$, $SO_2NH_2$, OH, phenoxy or $COOC_{1-4}$ alkyl, or
$R^8$ and B together with the nitrogen atom form a 5- to 7-membered saturated heterocycle, which can contain another oxygen, nitrogen or sulfur atom and can be substituted with $C_{1-4}$ alkyl, phenyl, benzyl or benzoyl or form an unsaturated 5-membered heterocycle, which can contain 1–3 N atoms and can be substituted with phenyl, $C_{1-4}$ alkyl or halogen, or
$R^7$ and A together with the nitrogen atom form a 5- to 7-membered saturated heterocycle, which can contain another oxygen, nitrogen or sulfur atom or forms an unsaturated 5-membered heterocycle, which can contain 1–3 N atoms,
m means 0, 1 or 2,
n and r mean 0, 1 to 6,
p and q mean 0 to 6,
$R^9$ and $R^{10}$ mean hydrogen or $C_{1-6}$ alkyl,
$R^{11}$ means $C_{1-6}$ alkyl, $-N_2$, $-NH-CH$, $-NH-CN$, $C_{6-10}$ aryl optionally substituted with halogen, $C_{1-4}$ alkyl or $CF_3$, or 5- or 6-membered heteroaryl with 1 to 4 nitrogen, sulfur or oxygen atoms that is optionally substituted with halogen, $C_{1-4}$ alkyl or $CF_3$;
$R^{12}$ and $R^{13}$ mean hydrogen, $C_{1-6}$ alkyl,-phenyl optionally substituted with halogen or $C_{1-4}$ alkyl, benzyl optionally substituted with halogen or $C_{1-4}$ alkyl or $C_{3-7}$ cycloalkyl,
$R^{14}$ means hydrogen, hydroxy, $C_{1-6}$ alkoxy, phenyl, $C_{1-6}$ alkyl optionally substituted with $CO_2H$, $CO_2C_{1-6}$ alkyl, hydroxy, $C_{1-4}$ alkoxy, halogen, $NR^{15}R^{16}$, $CONR^{12}R^{13}$, or phenyl, or $C_{2-6}$ alkenyl optionally substituted with phenyl, cyano, $CONR^{12}R^{13}$ or $CO_2C_{1-4}$ alkyl,
$R^{15}$ and $R^{16}$ mean hydrogen, $C_{1-6}$ alkyl, phenyl or benzyl or
$R^{15}$ and $R^{16}$ together with the nitrogen atom form a saturated 5-, 6-, or 7-membered ring, which can contain another nitrogen, oxygen or sulfur atom and can be substituted with $C_{1-4}$ alkyl, phenyl, benzyl or benzoyl, whereby if X=0, $R^6$ means methyl and $R^2$, $R^3$, $R^4$ and $R^5$ mean hydrogen, $R^1$ is not 6-((4-aminobenzyl)aminomethyl), 6-((4-dimethylaminobenzyl)aminomethyl), 6-((4-aminobenzyl)(tert-butyloxycarbonyl)aminomethyl), 6-((4-dimethylaminobenzyl)(tert-butyloxycarbonyl) aminomethyl).

The compounds of the formula can be present as tautomers, stereoisomers or geometric isomers. The invention also comprises all possible isomers, such as E- and Z-isomers, S- and R-enantiomers, diastereomers, racemates and mixtures thereof, including the tautomeric compounds of Formulas 1a and 1b

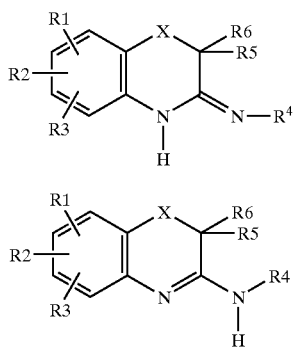

The physiologically compatible salts can be formed with inorganic and organic acids, such as, for example, oxalic acid, lactic acid, citric acid, fumaric acid, acetic acid, maleic acid, tartaric acid, phosphoric acid, HCl HBr, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, or octyl.

If alkyl radical U is substituted with halogen, it can be halogenated and perhalogenated in one or more places like, for example, trifluoromethyl and trifluoroethyl.

Alkenyl and alkynyl substituents preferably contain a double bond and are in each case straight-chain or branched. For example, the following radicals can be mentioned: vinyl, 2-propenyl, 1-propenyl, 2-butenyl, 1-butenyl, 3-butenyl, 2-methyl-2-propenyl, 2-pentenyl, 4-hexenyl, ethinyl, 1-propinyl, 2-propinyl, 1-butinyl, 2-butinyl.

Cycloalkyl is defined respectively as cyclopropyl, cyclobutyl, cyclopentyl, cyclohexyl or cycloheptyl. As a bicyclic compound, for example, bicycloheptane and bicyclooctane can be mentioned.

Halogen means respectively fluorine, chlorine, bromine or iodine.

Aryl is defined respectively as naphthyl or phenyl, which can be substituted by the same or a different component in one to three places.

As heteroaryl radicals, which can be bonded via the heteroatom or a carbon atom, for example, the following 5- and 6-ring heteroaromatic compounds can be mentioned:

Imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline. As a heteroaryl radical, 2-$C_{1-6}$ alkyl-3-amino-1,4-benzoxazine and 2-$C_{1-6}$-alkyl-3-keto-1,4-benzoxazine are also suitable.

As a preferred embodiment for $R^{11}$ in the meaning of heteroaryl, thienyl can be considered.

As a saturated heterocycle, for example, piperidine, pyrrolidine, morpholine, thiomorpholine, hexahydroazepine and piperazine can be mentioned. The heterocycle can be substituted in 1 to 3 places with $C_{1-4}$ alkyl or a phenyl, benzyl or benzoyl radical that is optionally substituted with halogen. For example, there can be mentioned: N-methyl-piperazine, 2,6-dimethylmorpholine, phenylpiperazine or 4-(4-fluorobenzoyl)-piperidine.

If —$NR^8B$ or —$NR^7$—A— together with the nitrogen atom form an unsaturated heterocycle, for example, imidazole, pyrrole, pyrazole and triazole can be mentioned.

Simple substitution is preferred for substituents $R^5$ and $R^6$ in 2-position of the oxazine or thiazine, whereby substituent $R^6$ in particular means $C_{1-6}$ alkyl and substituent $R^5$ in particular means hydrogen.

Substituent q can be linked via a C atom at any point or optionally via an N atom.

If $R^1$ and $R^2$ together with two adjacent carbon atoms form a ring, the latter can be in 5,6- or 6,7- or 7,8-position of the benzoxazine or benzothiazine and has the formula

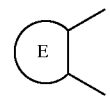

in which

E means a saturated or unsaturated $C_{3-8}$ alkylene radical, which is substituted in 1 to 2 places with —$(CHR^9)_r$— $NR^7$—A—$NR^8B$ and optionally in 1–2 places with $C_{1-4}$ alkyl and in which 1 or 2 $CH_2$ groups can be replaced by oxygen, carbonyl or its derivative, whereby the alkylene radical can contain a slightly condensed benzene radical, such as, for example, indan, or can be present as a bicyclic compound, such as, for example, bicycloheptane.

As structures of E, there can be mentioned, for example:

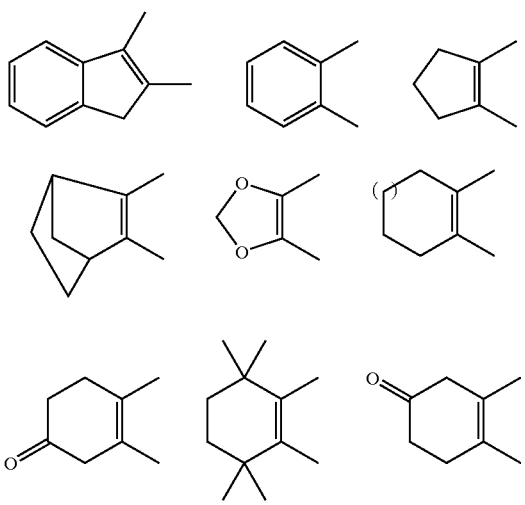

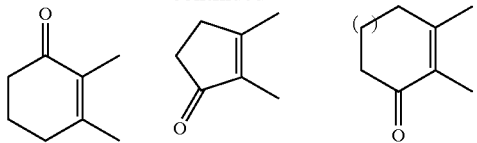

As carbonyl derivatives, for example, =NOH, =N—OC$_{1-6}$ alkyl, =NH—NH$_2$, =N—NH-phenyl are suitable.

Preferably, two adjacent carbon atoms of the aromatic compound are linked with C$_{1-6}$ alkylene to a 3- to 8-membered, especially a 5- to 6-membered unsaturated ring, which is substituted in any position; in particular E means saturated or unsaturated C$_{5-6}$ alkylene, which is substituted with —(CHR$^9$)$_r$—NR$^7$—A—NR$^8$B, whereby r in particular means zero.

Acyl radical R$^4$ is derived from straight-chain or branched aliphatic carboxylic acids, such as, for example, formic acid, acetic acid, propionic acid, butyric acid, trimethylacetic acid or caproic acid or from known benzenesulfonic acids, which can be substituted with halogen or C alkyl, and C alkanesulfonic acids, such as, for example, methanesulfonic acid, and p-toluenesulfonic acid.

Preferred embodiments of X are S and O.

In each case, R$^4$, R$^7$ and R$^8$ preferably mean hydrogen, and a preferred embodiment of R$^3$ is hydrogen.

The meaning of n preferably does not equate to zero.

Substituents R$^7$ and R$^8$ preferably mean hydrogen.

A preferred embodiment of A is especially straight-chain or branched C$_{1-6}$ alkylene or —(CH$_2$)$_p$—Q—(CH$_2$)$_q$, whereby p and q in each case especially mean 1–4.

Preferred embodiments of U are hydrogen, C$_{1-6}$ alkyl optionally substituted with halogen, C$_{3-7}$ cycloalkyl and phenyl, which can be substituted with halogen, C$_{1-4}$ alkyl, C$_{1-4}$ alkoxy, CF$_3$, NO$_2$, NH$_2$, N(C$_{1-4}$-alkyl)$_2$, cyano, CONH$_2$, —O—CH$_2$—O—, —O—(CH$_2$)$_2$—O—, SO$_2$NH$_2$, OH, phenoxy or COOC$_{1-4}$ alkyl.

The invention also relates to the use of the compounds according to the invention for the production of a pharmaceutical agent for treating diseases, which are induced by the action of nitrogen monoxide at pathological concentrations. These include neurodegenerative diseases, inflammatory diseases, auto-immune diseases, and cardiovascular diseases.

For example, there can be mentioned:

Cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, sleep disorders, schizophrenia, depression, stress, pain, migraine, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc.

Based on their profile of action, the compounds according to the invention are very well suited for inhibiting the neuronal NOS.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can also optionally be used subcutaneously, intramuscularly or intravenously, or topically in the form of aerosols or transdermal systems or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, plant oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethoxylated castor oil, are suitable.

As vehicle systems, surface-active adjuvants such as salts of bile acids or animal or plant phospholipids, but also mixtures thereof as well as liposomes or their components can also be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredient can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into two or more daily doses.

The NOS-inhibitory action of the compounds of formula I and their physiologically compatible salts can be determined according to the methods by Bredt and Snyder in Proc. Natl. Acad. Sci. USA (1989) 86, 9030–9033.

The production of the compounds according to the invention is carried out in that a compound of formula II or its salt

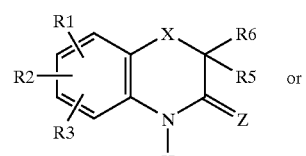

IIa

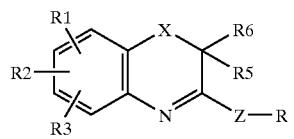

IIb in which
R$^1$, R$^2$, R$^3$, R$^5$, R$^6$ and X have the above-mentioned meaning, Z is oxygen or sulfur and R means C$_{1-6}$ alkyl, is reacted with ammonia or primary amines, whereby existing amino groups are optionally intermediately protected and optionally then acylated, the isomers are separated or the salts are formed.

The reaction with ammonia is possible under pressure in autoclaves with excess ammonia at low temperatures (−78° C.) or by stirring in methanol that is saturated with ammonia at room temperature. Thiolactams are preferably reacted. If the reaction is with amines, first the iminoethers or iminothioethers are produced from lactam or thiolactam as intermediate compounds (e,g., with methyl iodide or methyl sulfate), and the latter are reacted with or without isolation of the intermediate compounds with the corresponding amines or their salts.

As amino protective groups, for example, carbamates, such as tert-butoxycarbonyl, benzyloxycarbonyl or acetyl, are suitable.

In the precursor stages, optionally sulfides are oxidized, esters are saponified, acids are esterified, hydroxy groups are etherified or acylated, amines are acylated, alkylated, diazotized, halogenated, $NO_2$ is introduced or reduced, reacted with isocyanates or isothiocyanates, the isomers are separated or the salts are formed.

The saponification of an ester group can be done basically or acidically by hydrolysis being performed at room temperature or at an elevated temperature up to boiling temperature of the reaction mixture in the presence of alkali hydroxides in ethanol or other alcohols or with use of acids, such as, e.g., hydrochloric acid, and optionally salts of aminobenzoxazines or -thiazines being further processed.

The esterification of carboxylic acid is done in a way that is known in the art with diazomethane or the corresponding alcohol in acid or in the presence of an activated acid derivative. As activated acid derivatives, for example, acid chloride, -imidazolide or -anhydride are suitable.

The reduction of an ester group to alcohol is carried out in a way that is known in the art with DIBAH in suitable solvents at low temperatures. The reductive amination of a ketone or a benzaldehyde with amine while adding boron hydride provides benzylic amines. With suitably selected diamines, symmetrical or unsymmetrical amino compounds are obtained after identical or different aldehydes are added.

In addition, a nitro group or halogen, especially bromine, can be introduced by electrophilic, aromatic substitution. Mixtures that are produced in this case can be separated in the usual way, also using HPLC. If a nitrile is present, the latter can be saponified according to known processes or can be converted into the corresponding amine, tetrazole or amidoxime, or it is in a substituted amidine by attacking substituted anilines or amines.

The Friedel-Crafts acylation is used successfully in lactams of type IIa, and then the lactam can be converted selectively into the thiolactam, or the acylation product can be reductively aminated.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride can also be used, such as complex metal hydrides optionally in the presence of heavy metal salts. The ester group can be advantageously introduced before the reduction as in Formula V. For nitro groups, the reduction with zinc or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

Benzyl alcohols can be converted into corresponding benzyl halides as usual with methanesulfonyl chloride.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water or concentrated sulfuric acid as a solvent is also possible at temperatures of between −10° C. and 30° C.

The isomer mixtures can be separated into enantiomers or E/Z-isomers according to commonly used methods, such as, for example, crystallization, chromatography or salt formation. The enantiomers can also be obtained by chromatography on chiral phases as well as by stereoselective syntheses.

The production of the salts is carried out in the usual way, by a solution of the compound of Formula I—optionally also with protected amino groups—being mixed with the equivalent amount of acid or excess acid, which optionally is in solution, and the precipitate being separated or the solution being worked up in the usual way.

Nucleophilic substitution of benzyl halides with secondary amines yields the corresponding benzylamines.

Thiolactams of formula IIa (Z=S) are obtained from, for example, lactams with phosphorus pentasulfide ($P_4S_{10}$) or Lawesson's reagent (2,4-bis(4-methoxyphenyl)-1,3,2,4-dithiaphosphetane-2,4-disulfide) in suitable solvents, and compounds of Formula IIb can be obtained by, for example, reaction with Meerwein reagent (trimethyloxonium tetrafluoroborate).

If the production of the starting compounds is not described, the latter are known and commercially available or can be produced analogously to known compounds or according to processes that are described here.

The invention also relates to the intermediate compounds of Formulas IIa and IIb and their salts

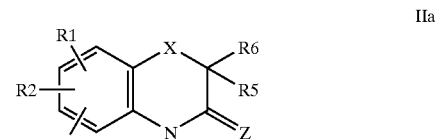

IIa

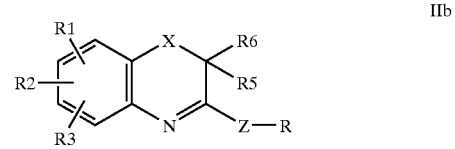

IIb in which $R^1$, $R^2$, $R^3$, $R^5$, $R^6$ and X have the above-mentioned meaning, Z is oxygen or sulfur and R means $C_{1-6}$ alkyl.

The production of the compounds of Formula IIa can be done, for example, in that a compound of Formula III

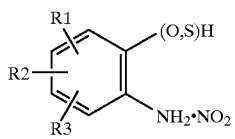

in which $R^1$ to $R^3$ have the above-mentioned meaning is reacted with a compound of Formula IV.

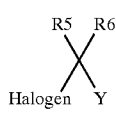

in which $R^5$ and $R^6$ have the above-mentioned meaning, and Y is a reactive carboxyl group such as acid halide, nitrile, carboxylic acid ester, and optionally is reductively cyclized, or in that a compound of Formula V

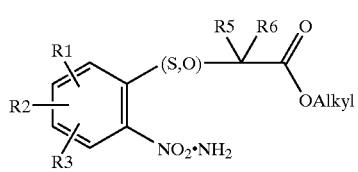

is reductively cyclized.

Aromatic thiols of type III are obtained, i.a., as described in Chem. Pharm. Bull. 1991, 39, 2888 and the literature that is mentioned there by rearrangement of the corresponding dimethylaminothiocarbamates.

The introduction of substituents $R^1$ to $R^3$ can be carried out in the stage of the compounds of Formula III or II.

For the production of compounds of Formula II, the aldehyde or the ketone of the corresponding 1,4-benzoxazine-3-one or 1,4-benzothiazine-3-one can be reductively aminated. This can also be done in two places with suitably selected diamines. Diamines can also be reacted with the aldehyde of 1,4-benzoxazin-3-one and simultaneously with suitably selected other aldehydes. If the introduction of a heteroaryl radical Q is desired, the corresponding halogen derivative can be substituted nucleophilically. If a primary or secondary amino group is present, it may be advantageous to protect the latter intermediately, for example by introduction of a tert-butoxycarbonyl group, which is usually cleaved according to the amidine formation. The production of pharmacologically active compounds from the intermediate products is carried out as described above.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents are respectively indicated and abbreviated as follows: $CDCl_3$ (chloroform), DMSO (dimethyl sulfoxide). Alterations are indicated in delta and ppm. Here: m means multiplet, several signals; s means singlet; d means doublet; dd means double doublet, etc.; tr means triplet; q means quartet; H means hydrogen protons; J means coupling constant. In addition, THF means tetrahydrofuran, DMF means N,N-dimethylformamide, MeOH means methanol, EE means ethyl acetate, ml means milliliter, and RT means room temperature. All solvents are p.A. grade, unless otherwise indicated. All reactions are performed under protective gas, unless these are aqueous solutions.

Below, the production of several precursors, intermediate products and products is described by way of example.

Starting Compounds

A1

The synthesis of 6-formyl-2-methyl-2H-1,4-benzoxazin-3-one is described in DE-198 26 232.9, as is that of 6-formyl-2-ethyl-2H-1,4-benzoxazin-3-one and 6-formyl-2-propyl-1,4-benzoxazin-3-one.

6-((3-Aminomethyl)-benzylaminomethyl)-2-methyl-2H-1,4-benzoxazin-3-one and 6-(meta-(N-[3-keto-2-methyl-2H-1,4-benzoxazin-6-yl]-methylaminomethyl)-benzylaminomethyl)-2-methyl-1,4-benzoxazin-3-one In a mixture of 4 ml of methanol and 2 ml of THF, 382 mg of 6-formyl-2-methyl-1,4-benzoxazin-3-one is dissolved and mixed with 136 mg of 3-(aminomethyl)-benzylamine. It is stirred for 30 minutes at room temperature, and then 101 mg of potassium borohydride is added. After 12 hours at room temperature, it is poured onto water, extracted three times with ethyl acetate, and the organic phase is washed with brine. It is dried with magnesium sulfate and concentrated by evaporation. 455 mg of crude product, which is provided with a protective group and then separated into individual compounds by chromatography, is obtained.

The following are produced in the same way:

6-((4-Aminomethyl)-benzylaminomethyl)-2-methyl-2H-1,4-benzoxazin-3-one and 6-(para-(N-[3-keto-2-methyl-2H-1,4-benzoxazin-6-yl]-methylaminomethyl)-benzylaminomethyl)-2-methyl-1,4-benzoxazin-3-one 6-(3-aminopropyl-aminomethyl)-2-methyl-2H-1,4-benzoxazin-3(4H)-one 6-(3-[N-methyl-amino]-propyl-aminomethyl)-2-methyl-2H-1,4-benzoxazin-3(4H)-one 6-(3-{[N-3-chlorobenzyl]-aminopropyl}-aminomethyl)-2-methyl-2H-1,4-benzoxazin-3(4H)-one 6-(4-{[N-3-chlorobenzyl]-amino-n-butyl}-aminomethyl)-2-methyl-2H-1,4-benzoxazin-3(4H)-one 6-(4-{[N-2-thienylmethyl]-amino-n-butyl}-aminomethyl)-2-methyl-2H-1,4-benzoxazin-3(4H)-one 6-(5-{[N-3-chlorobenzyl]-amino-n-pentyl}-aminomethyl)-2-methyl-2H-1,4-benzoxazin-3(4H)-one 6-(6-{[N-3-chlorobenzyl]-amino-n-hexyl}-aminomethyl)-2-methyl-2H-1,4-benzoxazin-3(4H)-one 6-(4-{[N-4-fluorobenzyl]-amino-n-butyl}-aminomethyl)-2-methyl-2H-1,4-benzoxazin-3(4H)-one 6-(4-{[N-3-trifluorobenzyl]-amino-n-butyl}-aminomethyl)-2-methyl-2H-1,4-benzoxazin-3(4H)-one 6-(4-{[N-ortho-hydroxybenzyl]-amino-n-butyl}-aminomethyl)-2-methyl-2H-1,4-benzoxazin-3(4H)-one 6-(5-{[N-isopropyl]-amino-n-pentyl}-aminomethyl)-2-methyl-2H-1,4-benzoxazin-3(4H)-one 6-(4-{[N-isopropyl]-amino-n-butyl}-aminomethyl)-2-methyl-2H-1,4-benzoxazin-3(4H)-one 6-(3-{[N-isopropyl]-amino-n-propyl}-aminomethyl)-2-methyl-2H-1,4-benzoxazin-3(4H)-one 6-(4-{[N-cyclopropyl]-amino-n-butyl}-aminomethyl)-2-methyl-2H-1,4-benzoxazin-3(4H)-one 6-(4-{[N-cyclopentyl]-amino-n-butyl}-aminomethyl)-2-methyl-2H-1,4-benzoxazin-3(4H)-one 6-(4-{[N-(cyclohexyl)-methyl]-amino-n-butyl}-aminomethyl)-2-methyl-2H-1,4-benzoxazin-3(4H)-one 6-(4-{[N-(cyclopropyl)-methyl]-amino-n-butyl}-aminomethyl)-2-methyl-2H-1,4-benzoxazin-3(4H)-one 6-(4-{[N-2,2,2-trifluoroethyl]-amino-n-butyl}-aminomethyl)-2-methyl-2H-1,4-benzoxazin-3(4H)-one 6-(4-{[N-4,4,4-trifluorobutyl]-amino-n-butyl}-aminomethyl)-2-methyl-2H-1,4-benzoxazin-3(4H)-one Produced from 6-keto-6,7,8,9-tetrahydro-2-methyl-2H-naphth [2,3-b]-1,4-oxazin-3(4H)-one are:

6-{[4-Amino-n-butyl]-amino}-6,7,8,9-tetrahydro-2-methyl-2H-naphth[2,3-b]-1,4-oxazin-3(4H)-one 6-{[5-amino-n-pentyl]-amino}-6,7,8,9-tetrahydro-2-methyl-2H-naphth[2,3-b]-1,4-oxazin-3(4H)-one 6-{3-aminomethyl-benzylamino}-6,7,8,9-tetrahydro-2-methyl-2H-naphth[2,3-b]-1,4-oxazin-3(4H)-one 6-{[4-(N-isopropylamino)-n-butyl]-amino}-6,7,8,9-tetrahydro-2-methyl-2H-naphth[2,3-b]-1,4-oxazin-3(4H)-one 6-{[5-(N-isopropylamino)-n-pentyl]-amino}-6,7,8,9-tetrahydro-2-methyl -2H-naphth[2,3-b]-1,4-oxazin-3(4H)-one Produced from 6-keto-6,7-trimethylene-2-methyl-2H-1,4-benzoxazin-3(4H)-one are:

6-{[4-Amino-n-butyl]-amino}-6,7-trimethylene-2-methyl-2H-1,4-benzoxazin-3(4H)-one 6-{[5-amino-n-pentyl]-amino}-6,7-trimethylene-2-methyl-2H-1,4-benzoxazin-3(4H)-one 6-{[4-(N-isopropylamino)-n-butyl]-amino}-6,7-trimethylene-2-methyl-2H-1,4-benzoxazin-3(4H)-one 6-{[5-(N-isopropylamino)-n-pentyl]-amino}-6,7-trimethylene-2-methyl-2H-1,4-benzoxazin-3(4H)-one 6-{3-aminomethyl-benzyl-amino}-6,7-trimethylene-2-methyl-2H-1,4-benzoxazin-3(4H)-one From 1,3-cyclohexyl-bis-methylamine:

6-((3-Aminomethyl-cyclohex-1-yl)-methylaminomethyl)-2-methyl-2H-1,4-benzoxazin-3-on and 6-(3-[N-keto-2-methyl-2H-1,4-benzoxazin-6-yl]-methylaminomethyl)-cyclohex-1-ylmethylaminomethyl)-2-methyl-1,4-benzoxazin-3-one From diamines:

6-((omega-Aminobutylaminomethyl)-2-methyl-2H-1,4-benzoxazin-3-one 6-((omega-aminopentylaminomethyl)-2-methyl-2H-1,4-benzoxazin-3-one 6-((omega-aminohexylaminomethyl)-2-methyl-2H-1,4-benzoxazin-3-one

A2

6-((3-[4-Nitrobenzyl]-aminomethyl)-benzylaminomethyl)-2-methyl-2H-1,4-benzoxazin-3(4H)-one In a mixture of 10 ml of methanol and 5 ml of THF, 573 mg of 6-formyl-2-methyl-1,4-benzoxazin-3-one is dissolved and mixed with 0.382 ml of 3-(aminomethyl)-benzylamine and 438 mg of p-nitrobenzaldehyde. It is stirred for 1 hour at room temperature, and then 173 mg of potassium borohydride is added. After 4 hours at room temperature, it is poured onto water, extracted three times with ethyl acetate, and the organic phase is washed with brine. It is dried with magnesium sulfate and concentrated by evaporation. 1.18 g of crude product, which is provided with a protective group, is obtained.

The following are produced in the same way:

6-((3-[2-Methylbenzyl]-aminomethyl)-benzylaminomethyl)-2-methyl-2H-1,4-benzoxazin-3-one 6-((3-[2,4-dichlorobenzyl]-aminomethyl)-benzylaminomethyl)-2-methyl-2H-1,4-benzoxazin-3-one 6-((3-[3-chlorobenzyl]-aminomethyl)-benzylaminomethyl)-2-methyl-2H-1,4-benzoxazin-3-one 6-((3-[3,4-dichlorobenzyl]-aminomethyl)-benzylaminomethyl)-2-methyl-2H-1,4-benzoxazin-3-one 6-((3-benzylaminomethyl)-benzylaminomethyl)-2-methyl-2H-1,4-benzoxazin-3-one

B 6-(3-[tert-Butyloxycarbonyl]aminomethyl)-benzyl-(tert-butyloxycarbonyl)-aminomethyl)-2-methyl-2H-1,4-benzoxazin-3-one 1 and 6-(meta-(N-[3-keto-2-methyl-2H-1,4-benzoxazin-6-yl]-methyl-(tert-butyloxycarbonyl)-aminomethyl)-benzyl-(tert-butyloxycarbonyl)-aminomethyl)-2-methyl-2H-1,4-benzoxazin-3-one 2

The products are obtained by reacting the mixture of 440 mg of 6-((3-amino-methyl)-benzylaminomethyl)-2-methyl-1,4-benzoxazin-3-one and 6-(meta-(N-[3-keto-2-methyl-2H-1,4-benzoxazin-6-yl]-methylaminomethyl)-benzylaminomethyl)-2-methyl-1,4-benzoxazin-3-one in 15 ml of dichloromethane while adding 0.38 ml of triethylamine and 476 mg of di-tert-butyldicarbonate After 12 hours at room temperature, it is diluted with dichloromethane, washed with sodium bicarbonate and then with brine. The organic phase is dried and concentrated by evaporation. After column chromatography with hexane/ethyl acetate, 160 mg of 1 and 257 mg of 2 result.

1

[1H]-NMR (CDCl$_3$): 7.27 m 1H, 6.5 to 7.18 m 7H, 5 broad 1H, 4.62 q 1H, 4.2 to 4.4 m broad 5H, 1.58 d 3H, 1.50 s 9H, 1.48 s 9H. MS (ei) 511 m/z M+.

2

[1H]-NMR (CDC$_3$): 7.1 to 7.3 m broad and 6.6 to 6.9 m together with 10H, 4.63 q 2H, 4.3 to 4.4 m broad 8H, 1.6 d 6H, 1.50 s 18H. MS (ei) 630, 586, 574, 529 m/z fragments.

The following are produced in the same way:

6-((4-(tert-Butyloxycarbonyl)-aminomethyl)-benzyl-(tert-butyloxycarbonyl)-aminomethyl)-2-methyl-1,4-benzoxazin-3-one and 6-(para-(N-[3-keto-2-methyl-2H-1,4-benzoxazin-6-yl]-methyl-(tert-butyloxycarbonyl)-aminomethyl)-benzyl-(tert-butyloxycarbonyl)-aminomethyl)-2-methyl-1,4-benzoxazin-3-one 6-(3-(tert-Butyloxycarbonyl)-aminomethyl-cyclohex-1-yl)-methyl-(tert-butyloxycarbonyl)aminomethyl)-2-methyl-1,4-benzoxazin-3-one and 6-(3-(N-[3-keto-2-methyl-2H-1,4-benzoxazin-6-yl]-methyl-(tert-butyloxycarbonyl)-aminomethyl)-cyclohex-1-ylmethyl-(tert-butyloxycarbonyl)-aminomethyl)-2-methyl-1,4-benzoxazin-3-one 6-((omega-(tert-butyloxycarbonyl)-aminobutyl-(tert-butyloxycarbonyl)-aminomethyl)-2-methyl-1,4-benzoxazin-3-one 6-((omega-(tert-butyloxycarbonyl)-aminopentyl-(tert-butyloxycarbonyl)-aminomethyl)-2-methyl-1,4-benzoxazin-3-one 6-((omega-(tert-butyloxycarbonyl)-aminohexyl-(tert-butyloxycarbonyl)-aminomethyl)-2-methyl-1,4-benzoxazin-3-one 6-((3-[4-nitrobenzyl]-(tert-butyloxycarbonyl)-aminomethyl)-benzyl(tert-butyloxycarbonyl)-aminomethyl)-2-methyl-1 4-benzoxazin-3-one 6-((3-[2-methylbenzyl]-(tert-butyloxycarbonyl-aminomethyl)-benzyl(tert-butyloxy-carbonyl)-aminomethyl)-2-methyl-1,4-benzoxazin-3-one 6-((3-[2,4-dichlorobenzyl]-(tert-butyloxycarbonyl)-aminomethyl)-benzyl(tert-butyloxy-carbonyl)-aminomethyl)-2-methyl-1,4-benzoxazin-3-one 6-((3-[3-chlorobenzyl]-(tert-butyloxycarbonyl)-aminomethyl)-benzyl(tert-butyloxy-carbonyl)-aminomethyl)-2-methyl-1,4-benzoxazin-3-one 6-((3-[3,4-dichlorobenzyl]-(tert-butyloxycarbonyl)-aminomethyl)-benzyl(tert-butyloxy-carbonyl)-aminomethyl)-2-methyl-1,4-benzoxazin-3-one 6-((3-benzyl(tert-butyloxycarbonyl)-aminomethyl)-benzyl(tert-butyloxycarbonyl)-aminomethyl)-2-methyl-1,4-benzoxazin-3-one 6-(3-(tert-Butyloxycarbonyl)-aminopropyl-(tert-butyloxycarbonyl)-aminomethyl)-2-methyl-2H-1,4-benzoxazin-3(4H)-one 6-(3-[N-methyl-(tert-butyloxycarbonyl)-amino]-propyl-(tert-butyloxycarbonyl)-aminomethyl)-2-methyl-2H-1,4-benzoxazin-3(4H)-one 6-(3-{[N-3-chlorobenzyl]-(tert-butyloxycarbonyl)-aminopropyl}-(tert-butyloxycarbonyl)-aminomethyl-2-methyl-2H-1,4-benzoxazin-3(4H)-one 6-(4-{[N-3-chlorobenzyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-2-thienylmethyl]-(tert-butyloxycarbonyl)-amino-n-butyl}-(tert-butyloxycarbonyl)-aminomethyl)-2-methyl-2H-1,4-benzoxazin-3(4H)-one 6-(5-{[N-3-chlorobenzyl]-(tert-butyloxycarbonyl)-amino-n-pentyl}-(tert-butyloxycarbonyl)-aminomethyl)-2-methyl-2H-1,4-benzoxazin-3(4H)-one 6-(6-{[N-3-chlorobenzyl]-(tert-butyloxycarbonyl)-amino-n-hexyl}-(tert-butyloxycarbonyl)-aminomethyl)-2-methyl-2H-1,4-benzoxazin-3(4H)-one 6-(4-{[N-4-fluorobenzyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-3-trifluorobenzyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-ortho-hydroxybenzyl]-(tert-butyloxycarbonyl)-amino-n-butyl}-(tert-butyloxycarbonyl)-aminomethyl)-2-methyl-2H-1,4-benzoxazin-3(4H)-one 6-(5-{[N-isopropyl]-(tert-butyloxycarbonyl)amino-n-pentyl}-(tert-butyloxycarbonyl)-aminomethyl)-2-methyl-2H-1,4-benzoxazin-3(4H)-one 6-(4-{[N-isopropyl]-(tert-butyloxycarbonyl)-amino-n-butyl}-(tert-butyloxycarbonyl)-aminomethyl)-2-methyl-2H-1,4-benzoxazin-3(4H)-one 6-(3-{[N-isopropyl]-(tert-butyloxycarbonyl)-amino-n-propyl}-(tert-butyloxycarbonyl)-aminomethyl)-2-methyl-2H-1,4-benzoxazin-3(4H)-one 6-(4-{[N-cyclopropyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-cyclopentyl]-(tert-butyloxycarbonyl)-amino-n-butyl}-(tert-butyloxycarbonyl)-aminomethyl)-2-methyl-2H-14 benzoxazin-3(4H)-one 6-(4-{[N-(cyclohexyl)-methyl]-(tert-butyloxycarbonyl)-amino-n-butyl}(tert-butyloxycarbonyl)-aminomethyl)-2-methyl-2H-1,4-benzoxazin-3(4H)-one 6-(4-{[N-(cyclopropyl)-methyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-2,2,2-trifluoroethyl]-(tert-butyloxycarbonyl)-amino-n-butyl}-(tert-butyloxycarbonyl)-aminomethyl)-2-methyl-2H-1,4-benzoxazin-3(4H)-one 6-(4-{[N-4,4,4-trifluorobutyl]-(tert-butyloxycarbonyl)-amino-n-butyl}-(tert-butyloxycarbonyl)-aminomethyl)-2-methyl-2H-1,4-benzoxazin-3(4H)-one 6-{[4-(tert-butyloxycarbonyl)-amino-n-butyl]-(tert-butyloxycarbonyl)-amino}-6,7,8,9-tetrahydro-2-methyl-2H-naphth [2,3-b]-1,4-oxazin-3(4H)-one 6-{[5-(tert-butyloxycarbonyl)-amino-n-pentyl]-(tert-butyloxycarbonyl)-amino}-6,7,8,9-tetrahydro-2-methyl-2H-naphth [2,3-b]-1,4-oxazin-3(4H)-one 6-3-{(tert-butyloxycarbonyl)-aminomethyl-benzyl(tert-butyloxycarbonyl)-amino)-6,7,8,9-tetrahydro-2-methyl-2H-naphth [2,3-b]-1,4-oxazin-3(4H)-one 6-{[4-(N-isopropyl(tert-butyloxycarbonyl)-amino)-n-butyl]-(tert-butyloxycarbonyl)-amino}-6,7,8,9-tetrahydro-2-methyl-2H-naphth [2,3-b]-1,4-oxazin-3(4H)-one 6-{[5-(N-isopropyl(tert-butyloxycarbonyl)-amino)-n-pentyl]-(tert-butyloxycarbonyl)-amino}-6,7,8,9-tetrahydro-2-methyl-2H-naphth [2,3-b]-1,4-oxazin-3(4H)-one 6-{[4-(tert-butyloxycarbonyl)-amino-n-butyl}-(tert-butyloxycarbonyl)-amino}-6,7-trimethylene-2-methyl-2H-1,4-benzoxazin-3(4H)-one 6-{[5-(tert-butyloxycarbonyl)-amino-n-pentyl]-(tert-butyloxycarbonyl)-amino}-6,7-trimethylene-2-methyl-2H-1,4-benzoxazin-3(4H)-one 6-{[4-(N-isopropyl(tert-butyloxycarbonyl)-amino)-n-butyl]-(tert-butyloxycarbonyl)-amino}-6,7-trimethylene-2-methyl-2H-1,4-benzoxazin-3(4H)-one 6-{[5-(N-isopropyl(tert-butyloxycarbonyl)-amino)-n-pentyl]-(tert-butyloxycarbonyl)-amino}-6,7-trimethylene-2-methyl-2H-1,4-benzoxazin-3(4)-one 6-{3-(tert-butyloxycarbonyl)-aminomethyl-benzyl-tert-butyloxycarbonyl)-amino}-6,7-trimethylene-2-methyl-2H-1,4-benzoxazin-3(4H)-one

C 6-((3-[tert-Butyloxycarbonyl]-aminomethyl)-benzyl-(tert-butyloxycarbonyl)-aminomethyl)-2-methyl-1,4-benzoxazine-3(4H)-thione 192 mg of Lawesson's reagent is added at room temperature to 150 mg of 6-((3-[tert-butyloxycarbonyl]-aminomethyl)-benzyl-(tert-butyloxycarbonyl)-aminomethyl)-2-methyl-1,4-benzoxazin-3-one in 12 ml of dimethoxyethane, and it is stirred for 3 more hours. After concentration by evaporation and column chromatography with hexane/ethyl acetate 4:1, 140 mg of product results. The yield is 90%.

MS (ei) 527 (M+) 471, 454, 427, 415, 370, 338 m/z fragments.

The following are produced in the same way:

6-(meta-(N-[3-Thio-2-methyl-2H-1,4-benzoxazin-6-yl]-methyl-(tert-butyloxycarbonyl)-aminomethyl)-benzyl-(tert-butyloxycarbonyl)-aminomethyl)-2-methyl-2H-1,4-benzoxazine-3(4H)-thione [MS (Cl—NH$_3$) 719 (M+H) yield 45%] at 3 equivalents of Lawesson's reagent together with 6-(meta-(N-[3-keto-2-methyl-2H-1,4-benzoxazin-6-yl]-methyl-(tert-butyloxycarbonyl)-aminomethyl)-benzyl-(tert-butyloxycarbonyl)-aminomethyl)-2-methyl)-2H-1,4-benzoxazine-3(4H)-thione Yield 14%.

6-((4-(tert-Butyloxycarbonyl)-aminomethyl)-benzyl-(tert-butyloxycarbonyl)-aminomethyl)-2-methyl-2H-1,4-benzoxazine-3(4H)-thione 6-(para-(N-[3-Thio-2-methyl-2H-1,4-benzoxazin-6-yl]-methyl-(tert-butyloxycarbonyl)-aminomethyl)-benzyl-(tert-butyloxycarbonyl)-aminomethyl)-2-methyl-2H-1,4-benzoxazine-3(4H)-thione 46% yield together with 6-(para-(N-[3-Keto-2-methyl-2H-1,4-benzoxazin-6-yl]-methyl-(tert-butyloxycarbonyl)-aminomethyl)-benzyl-(tert-butyloxycarbonyl)-aminomethyl)-2-methyl-2H-1,4-benzoxazine-3(4H)-thione 6-((3-(tert-Butyloxycarbonyl)-aminomethyl-cyclohex-1-yl)-methyl-(tert-butyloxycarbonyl)aminomethyl)-2-methyl-2H-1,4-benzoxazine-3(4H)-thione 6-(3-(N-[3-Thio-2-methyl1-2H-1,4-benzoxazin-6-yl]-methyl-(tert-butyloxycarbonyl)-aminomethyl)-cyclohex-1-ylmethyl-(tert-butyloxycarbonyl)-aminomethyl)-2-methyl-2H-1,4-benzoxazine-3(4H)-thione 6-((omega-(tert-Butyloxycarbonyl)-aminobutyl-(tert-butyloxycarbonyl)-aminomethyl)-2-methyl-2H-1,4-benzoxazine-3(4H)-thione 6-((omega-(tert-butyloxycarbonyl)-aminopentyl-(tert-butyloxycarbonyl)-aminomethyl)-2-methyl-1,4-benzoxazine-3(4H)-thione 6-((omega-(tert-butyloxycarbonyl)-aminohexyl-(tert-butyloxycarbonyl)-aminomethyl)-2-methyl-2H-1,4-benzoxazine-3(4H)-thione 6-((3-[4-nitrobenzyl]-(tert-butyloxycarbonyl)-aminomethyl)-benzyl(tert-butyloxycarbonyl)-aminomethyl)-2-methyl-2H-1,4-benzoxazine-3(4H)-thione 6-((3-[2-methylbenzyl]-(tert-butyloxycarbonyl)-aminomethyl)-benzyl(tert-butyloxycarbonyl)-aminomethyl)-2-methyl,-2H-1,4-benzoxazine-3(4H)-thione (6-(3-[2,4-dichlorobenzyl]-(tert-butyloxycarbonyl)-aminomethyl)-benzyl(tert-butyloxycarbonyl)-aminomethyl)-2-methyl-2H-1,4-benzoxazine-3(4H)-thione 6-((3-[3-chlorobenzyl]-(tert-butyloxycarbonyl)-aminomethyl)-benzyl(tert-butyloxycarbonyl)-aminomethyl)-2-methyl1–2H-1,4-benzoxazine-3(4H)-thione 6-((3-[3,4-dichlorobenzyl]-(tert-butyloxycarbonyl)-aminomethyl)-benzyl(tert-butyloxycarbonyl)-aminomethyl)-2-methyl-2H-1,4-benzoxazine-3(4H)-thione 6-((3-benzyl(tert-butyloxycarbonyl)-aminomethyl)-benzyl(tert-butyloxycarbonyl)-aminomethyl)-2-methyl-2H-1,4-benzoxazine-3(4H)-thione 6-(3-(tert-Butyloxycarbonyl)-aminopropyl-(tert-butyloxycarbonyl)-aminomethyl)-2-methyl-2H-1,4-benzoxazine-3(4H)-thione 6-(3-[N-methyl-(tert-butyloxycarbonyl)-amino]-propyl-(tert-butyloxycarbonyl)-aminomethyl)-2-methyl1–2H-1,4-benzoxazine-3(4H)-thione 6-(3-{[-3-chlorobenzyl]-(tert-butyloxycarbonyl)-aminopropyl}-(tert-butyloxycarbonyl)-aminomethyl)-2-methyl-2H-1,4-benzoxazine-3(4H)-thione 6-(4-{[N-3-chlorobenzyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-2-thienylmethyl]-(tert-butyloxycarbonyl)-amino-n-butyl}-(tert-butyloxycarbonyl)-aminomethyl)-2-methyl-2H-1,4-benzoxazine-3(4H)-thione 6-(5-{[N-3-chlorobenzyl]-(tert-butyloxycarbonyl)-amino-n-pentyl}-(tert-butyloxycarbonyl)-aminomethyl)-2-methyl-2H-1,4-benzoxazine-3(4H)-thione 6-(6-{[N-3-chlorobenzyl]-(tert-butyloxycarbonyl)-amino-n-hexyl}-(tert-butyloxycarbonyl)-aminomethyl)-2-methyl-2H-1,4-benzoxazine-3(4H)-thione 6-(4-{[N-4-fluorobenzyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-3-trifluorobenzyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-ortho-hydroxybenzyl]-(tert-butyloxycarbonyl)-amino-n-butyl}-(tert-butyloxycarbonyl)-aminomethyl)-2-methyl-2H-1,4-benzoxazine-3(4H)-thione 6-(5-{[N-isopropyl]-(tert-butyloxycarbonyl)-amino-n-pentyl}-(tert-butyloxycarbonyl)-aminomethyl)-2-methyl-2H-1,4-benzoxazine-3(4H)-thione 6-(4-{[N-isopropyl]-(tert-butyloxycarbonyl)-amino-n-butyl}-(tert-butyloxycarbonyl)-aminomethyl)-2-methyl-2H-1,4-benzoxazine-3(4H)-thione 6-(3-{[N-isopropyl]-(tert-butyloxycarbonyl)-amino-n-propyl}-(tert-butyloxycarbonyl)-aminomethyl)-2-methyl-2H-1,4-benzoxazine-3(4H)-thione 6-(4-{[N-cyclopropyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-cyclopentyl]-(tert-butyloxycarbonyl)-amino-n-butyl}-(tert-butyloxycarbonyl)-(aminomethyl)-2-methyl-2H-1,4-benzoxazine-3(4H)-thione 6-(4-{[N-(cyclohexyl)-methyl]-(tert-butyloxycarbonyl)-amino-n-butyl}-(tert-butyloxycarbonyl)-aminomethyl)-2-methyl-2H-1,4-benzoxazine-3(4H)-thione (6-(4-{[N-(cyclopropyl)-methyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-2,2,2-trifluoroethyl]-(tert-butyloxycarbonyl)-amino-n-butyl}-(tert-butyloxycarbonyl)-aminomethyl)-2-methyl-2H-1,4-benzoxazine-3(4H)-thione 6-(4-{[N-4,4,4-trifluorobutyl]-(tert-butyloxycarbonyl)-amino-n-butyl}-(tert-butyloxycarbonyl-aminomethyl)-2-methyl-2H-1,4-benzoxazine-3(4H)-thione 6-{[4-(tert-butyloxycarbonyl)-amino-n-butyl]-(tert-butyloxycarbonyl)-amino}-6,7,8,9-tetrahydro-2-methyl-2H-naphth[2,3-b]-1,4-oxazine-3(4H)-thione 6-{[5-(tert-butyloxycarbonyl)-amino-n-pentyl]-(tert-butyloxycarbonyl)-amino}-6,7,8,9-tetrahydro-2-methyl-2H-naphth[2,3-b]-1,4-oxazine-3(4H)-thione 6-{3-(tert-butyloxycarbonyl))-aminomethyl-benzyl(tert-butyloxycarbonyl)-amino}-6,7,8,9-tetrahydro-2-methyl-2H-naphth[2,3-b]-1,4-oxazine-3(4H)-thione 6-{[4-(N-isopropyl(tert-butyloxycarbonyl)-amino)-n-butyl]-(tert-butyloxycarbonyl)-amino}-6,7,8,9-tetrahydro-2-Methyl-2H-naphth[2,3-b]-1,4-oxazine-3(4H)-thione 6-{[5-(N-isopropyl(tert-butyloxycarbonyl)-amino6)-n-pentyl]-(tert-butyloxycarbonyl)-amino}-6,7,8,9-tetrahydro-2-methyl-2H-naphth[2,3-b]-1,4-oxazine-3(4H)-thione 6-{[4-(tert-butyloxycarbonyl)-amino-n-butyl]-(tert-butyloxycarbonyl)-amino}-6,7-trimethylene-2-methyl-2H-1,4-benzoxazine-3(4H)-thione 6-{[5-(tert-butyloxycarbonyl)-amino-n-pentyl]-(tert-butyloxycarbonyl)-amino}-6,7-trimethylene-2-methyl-2H-1,4-benzoxazine-3(4H)-thione 6-{[4-(N-isopropyl(tert-butyloxycarbonyl)-amino)-n-butyl]-(tert-butyloxycarbonyl)-amino}-6,7-trimethylene-2-methyl-2H-1,4-benzoxazine-3(4H)-thione 6-{[5-N-isopropyl(tert-butyloxycarbonyl)-amino)-n-pentyl]-(tert-butyloxycarbonyl)-amino}-6,7-trimethylene-2-methyl-2H-1,4-benzoxazine-3(4H)-thione 6-{3-(tert-butyloxycarbonyl)-aminomethyl-benzyl-(tert-butyloxycarbonyl)-amino}-6,7-trimethylene-2-methyl-2H-1,4-benzoxazine-3(4H)-thione

EXAMPLE 1

6-((3-[tert-Butyloxycarbonyl]-aminomethyl)-benzyl-(tert-butyloxycarbonyl)-aminomethyl)-3-amino-2-methyl-1,4-benzoxazine 140 mg of 6-((3-[tert-butyloxycarbonyl]-aminomethyl)-benzyl-(tert-butyloxy-carbonyl)-aminomethyl)-2-methyl-1,4-benzoxazine-3-thione is stirred in 50 ml of saturated ammonia solution in methanol (commercially available). After 1 day at room. temperature, the crude product is obtained after concentration by evaporation. Column chromatography with ethyl acetate purifies the product. A 75% yield results.

[1H]-NMR (DMSO): 7.30 dd 2H, 7.14 dd 2H, 7.08 d 1H, 6.6 to 6.75 m 4H including amidine NH, 4.62 q 1H, 4.35 s broad 2H, 4.22 s broad 2H, 4.15 s broad 2H, 1.42 s 9H, 1.40 s 9H, 1.28 d 3H.

MS (ei): 510 m/z (M+).

The following are produced in the same way:

6-(meta-(N-[3-Amino-2-methyl-2H-1,4-benzoxazin-6-yl]-methyl-(tert-butyloxycarbonyl)-aminomethyl)-benzyl- (tert-butyloxycarbonyl)-aminomethyl)-3-amino-2-methyl-2H-1,4-benzoxazine 95% yield.

[1H]-NMR (DMSO): 7.30 dd 1H, 7.10 m 3H, 6.6 to 6.75 m 10H including amidine NH, 4.64 q 2H, 4.30 s broad 4H, 4.21 s broad 4H, 1.42 s 18H, 1.29 d 6H.

MS (Cl—NH$_3$) 685 m/z (M+1)

6-(meta-(N-[3-Keto-2-methyl-2H-1,4-benzoxazin-6-yl]-methyl-(tert-butyloxycarbonyl)-aminomethyl)-benzyl-(tert-butyloxycarbonyl)-aminomethyl)-3-amino-2-methyl-2H-1,4-benzoxazine 90% yield MS (Cl—NH$_3$) 686 m/z (M+1)

6-((4-(tert-Butyloxycarbonyl)-aminomethyl)-benzyl-(tert-butyloxycarbonyl)-aminomethyl)-3-amino-2-methyl-2H-1,4-benzoxazine 6-(para-(N-[3-Amino-2-methyl-2H-1,4-benzoxazin-6-yl]-methyl-(tert-butyloxycarbonyl)-aminomethyl)-benzyl-(tert-butyloxycarbonyl)-aminomethyl)-3-amino-2-methyl-2H-1,4-benzoxazine 92%, [1H]-NMR (DMSO): 7.17 s 2H, 6.6 to 6.75 m 8H, 4.64 q 2H, 4.30 s broad 4H, 4.21 s broad 4H, 1.41 s 18H, 1.28 d 6H.

MS (Cl-thioglycerol) 685 m/z (M+1)

6-(para-(N-[3-Keto-2-methyl-2H-1,4-benzoxazin-6-yl]-methyl-(tert-butyloxycarbonyl)-aminomethyl)-benzyl-(tert-butyloxycarbonyl)-aminomethyl)-3-amino-2-methyl-2H-1,4-benzoxazine (6-((3-(tert-Butyloxycarbonyl)-aminomethyl-cyclohex-1-yl)-methyl-(tert-butyloxycarbonyl)aminomethyl)-3-amino-2-methyl-2H-1,4-benzoxazine MS (Cl-thioglycerol) 517 m/z (M+1)

6-(3-(N-[3-Amino-2-methyl-2H-1,4-benzoxazin-6-yl]-methyl-(tert-butyloxycarbonyl)-aminomethyl)-cyclohex-1-ylmethyl-(tert-butyloxycarbonyl)-aminomethyl)-3-amino-2-methyl-2H-1,4-benzoxazine 6-((omega-(text-butyloxycarbonyl)-aminobutyl-(tert-butyloxycarbonyl)-aminomethyl)-3-amino-2-methyl-2H-1,4-benzoxazine 6-((omega-(tert-butyloxycarbonyl)-aminopentyl-(tert-butyloxycarbonyl)-aminomethyl)-3-amino-2-methyl-2H-1,4-benzoxazine 6-((omega-(tert-butyloxycarbonyl)-aminohexyl-(tert-butyloxycarbonyl)-aminomethyl)-3-amino-2-methyl-2H-1,4-benzoxazine 6-((3-[4-nitrobenzyl]-(tert-butyloxycarbonyl)-aminomethyl)-benzyl(tert-butyloxycarbonyl)-aminomethyl)-3-amino-2-methyl-2H-1,4-benzoxazine 6-((3-[2-methylbenzyl]-(tert-butyloxycarbonyl)-aminomethyl-benzyl(tert-butyloxycarbonyl)-aminomethyl)-3-amino-2-methyl-2H-1,4-benzoxazine 6-((3-[2,4-dichlorobenzyl]-(tert-butyloxycarbonyl)-aminomethyl)-benzyl(tert-butyloxycarbonyl)-aminomethyl)-3-amino-2-methyl-2H-1 4-benzoxazine 6-((3-[3-chlorobenzyl]-(tert-butyloxycarbonyl)-aminomethyl)-benzyl(tert-butyloxycarbonyl)-aminomethyl)-3-amino-2-methyl-2H-1,4-benzoxazine 6-((3-[3,4-dichlorobenzyl]-(tert-butyloxycarbonyl)-aminomethyl)-benzyl(tert-butyloxycarbonyl)-aminomethyl)-3-amino-2-methyl-2H-1,4-benzoxazine 6-((3-benzyl(tert-butyloxycarbonyl)-aminomethyl)-benzyl(tert-butyloxycarbonyl)-aminomethyl)-3-amino-2-methyl-2H-1,4-benzoxazine 6-(3-(tert-Butyloxycarbonyl)-aminopropyl-(tert-butyloxycarbonyl)-aminomethyl)-3-amino-2-methyl-2H-1,4-benzoxazine 6-(3-[N-methyl-(tert-butyloxycarbonyl)-amino]-propyl-tert-butyloxycarbonyl)-aminomethyl)-3-amino-2-methyl-2H-1,4-benzoxazine 6-{[N-3-chlorobenzyl]-(tert-butyloxycarbonyl)-aminopropyl}-(tert-butyloxycarbonyl)-aminomethyl)-3-amino-2-(methyl-2H-1,4-benzoxazine 6-(4-{[N-3-chlorobenzyl]-(tert-butyloxycarbonyl)-amino-n-butyl}-(tert-butyloxycarbonyl)-aminomethyl)-3-amino-2-methyl-2H-1,4-benzoxazine 6-(4-{[N-2-thienylmethyl]-(tert-butyloxycarbonyl)-amino-n-butyl}-(tert-butyloxycarbonyl)-aminomethyl)-3-amino-2-methyl-2H-1,4-benzoxazine 6-(5-{[N-3-chlorobenzyl]-(tert-butyloxycarbonyl)-amino-n-pentyl}-(tert-butyloxycarbonyl)-aminomethyl)-3-amino-2-methyl-2H-1,4-benzoxazine

6-(6-{[N-3-chlorobenzyl]-(tert-butyloxycarbonyl)-amino-n-hexyl}-(tert-butyloxycarbonyl)-aminomethyl)-3-amino-2-methyl-2H-1,4-benzoxazine 6-(4-{[N-4-fluorobenzyl]-(tert-butyloxycarbonyl)-amino-n-butyl}-(tert-butyloxycarbonyl)-aminomethyl)-3-amino-2-methyl-2H-1,4-benzoxazine 6-(4-{[N-3-trifluorobenzyl]-(tert-butyloxycarbonyl)-amino-n-butyl}-(tert-butyloxycarbonyl)-aminomethyl)-3-amino-2-methyl-2H-1,4-benzoxazine 6-(4-{[N-ortho-hydroxybenzyl]-(tert-butyloxycarbonyl)-amino-n-butyl)-(tert-butyloxycarbonyl-aminomethyl)-3-amino-2-methyl-2H-1,4-benzoxazine 6-(5-{[N-isopropyl]-(tert-butyloxycarbonyl)-amino-n-pentyl)-(tert-butyloxycarbonyl)-aminomethyl)-3-amino-2-methyl-2H-1,4-benzoxazine 6-(4-{[N-isopropyl]-(tert-butyloxycarbonyl)-amino-n-butyl}-(tert-butyloxycarbonyl)-aminomethyl)-3-amino-2-methyl-2H-1,4-benzoxazine 6-(3-{[N-isopropyl]-(tert-butyloxycarbonyl)-amino-n-propyl}-(tert-butyloxycarbonyl)-aminomethyl)-3-amino-2-methyl-2H-1,4-benzoxazine 6-(4-{[N-cyclopropyl]-(tert-butyloxycarbonyl)-amino-n-butyl}-(tert-butyloxycarbonyl)-aminomethyl}-3-amino-2-methyl-2H-1,4-benzoxazine 6-(4-{[N-cyclopentyl]-(tert-butyloxycarbonyl)-amino-n-butyl}-(tert-butyloxycarbonyl)-aminomethyl)-3-amino-2-methyl-2H-1,4-benzoxazine 6-(4-{[N-(cyclohexyl)-methyl]-(tert-butyloxycarbonyl)-amino-n-butyl}-(tert-butyloxycarbonyl)-aminomethyl)-3-amino-2-methyl-2H-1,4-benzoxazine 6-(4-{[N-(cyclopropyl)-methyl]-(tert-butyloxycarbonyl)-amino-n-butyl}-(tert-butyloxycarbonyl)-aminomethyl)-3-amino-2-methyl-2H-1,4-benzoxazine 6-(4-[[N-2,2,2-trifluoroethyl]-(tert-butyloxycarbonyl)-amino-n-butyl}-(tert-butyloxycarbonyl)-aminomethyl)-3-amino-2-methyl-2H-1,4-benzoxazine 6-(4-{[N-4,4,4-trifluorobutyl]-(tert-butyloxycarbonyl)-amino-n-butyl}-(tert-butyloxycarbonyl)-aminomethyl)-3-amino-2-methyl-2H-1,4-benzoxazine 6-{[4-(tert-butyloxycarbonyl)-amino-n-butyl]-(tert-butyloxycarbonyl)-amino}-6,7,8,9-tetrahydro-3-amino-2-methyl-2H-naphth [2,3-b]-1,4-oxazine 6-{[5-(tert-butyloxycarbonyl)-amino-n-pentyl]-(tert-butyloxycarbonyl)-amino}-6,7,8,9-tetrahydro-3-amino-2-methyl-2H-naphth [2,3-b]-1,4-oxazine 6-{3-(tert-butyloxycarbonyl)-aminomethyl-benzyl(tert-butyloxycarbonyl)-amino}-6,7,8,9-tetrahydro-3-amino-2-methyl-2H-naphth[2,3-b]-1,4-oxazine 6-{[4-(N-isopropyl(tert-butyloxycarbonyl)-amino)-n-butyl]-(tert-butyloxycarbonyl)-amino}-6,7,8,9-tetrahydro-3-amino-2-methyl-2H-naphth[2,3-b]-1,4-oxazine 6-{[5-(N-isopropyl(tert-butyloxycarbonyl)-amino)-n-pentyl]-(tert-butyloxycarbonyl)-amino}-6,7,8,9-tetrahydro-3-amino-2-methyl-2H-naphth[2,3-b]-1,4-oxazine 6-{[4-(tert-butyloxycarbonyl)-amino-n-butyl]-(tert-butyloxycarbonyl)-amino}-6,7-trimethylen-3-amino-2-methyl-2H-1,4-benzoxazine 6-{[5-(tert-butyloxycarbonyl)-amino-n-pentyl]-(tert-butyloxycarbonyl)-amino}-6,7-trimethylen-3-amino-2-methyl-2H-1,4-benzoxazine 6-{[4-(N-isopropyl(tert-butyloxycarbonyl)-amino)-n-butyl]-(tert-butyloxycarbonyl)-amino}-6,7-trimethylen-3-amino-2-methyl-2H-1,4-benzoxazine 6-{[5-(N-isopropyl(tert-butyloxycarbonyl)-amino)-n-pentyl]-(tert-butyloxycarbonyl)-amino}-6,7-trimethylen-3-amino-2-methyl-2H-1,4-benzoxazine 6-{3-(tert-butyloxycarbonyl)-aminomethyl-benzyl-(tert-butyloxycarbonyl)-amino}-6,7-trimethylen-3-amino-2-methyl-2H-1,4-benzoxazine

EXAMPLE 2

6-((3-Aminomethyl)-benzyl-aminomethyl)-3-amino-2-methyl-2H-1,4-benzoxazine trihydrochloride 95 mg of 6-((3-[tert-butyloxycarbonyl]-aminomethyl)-benzyl-(tert-butyloxycarbonyl)-aminomethyl)-3-amino-2-methyl-1,4-benzoxazine is stirred into 3 ml of dioxane with 2 ml of 4N hydrochloric acid (solution in dioxane). After 12 hours, it is diluted with some ethyl acetate, the crystals are suctioned off, washed with a little ethyl acetate and dried in a vacuum. 66 mg of product (92% yield) is obtained.

[1H]-NMR (DMSO): 9.9 broad, 9.5 broad, 8.5 broad s, 7.37 to 7.70 m 6 H, 7.11 d 1H, 5.36 q 1H, 4.15 broad 2H, 4.14 broad 2H, 4.04 broad 2H, 1.50 d 3H.

The following are produced in the same way:

6-(meta-(N-[3-Keto-2-methyl-2H-1,4-benzoxazin-6-yl]-methyl-aminomethyl)-benzyl-aminomethyl)-3-amino-2-methyl-2H-1,4-benzoxazine trihydrochloride Yield 99%

[1H]-NMR (DMSO): 9.9 broad, 9.7 broad, 7.0 to 7.75 m 10H, 5.33 q 1H, 4.70 q 1H, 4.15 broad 4H, 4.1 m 4H, 1.50 d 3H, 1,44 d 3H.

6-(meta-(N-[3-Amino-2-methyl-2H-1,4-benzoxazin-6-yl]-methyl-aminomethyl)-benzyl-aminomethyl)-3-amino-2-methyl-2H-1,4-benzoxazine trihydrochloride (HCl content not determined)

Yield 87%.

[1H]-NMR (DMSO): 9.9 broad, 9.5 broad, 7.38 dd 2H, 7.5m 3H, 7.65 dd 2H, 7.75 s 1H, 7.11 d 2H, 5.33 q 2H, 4.15 broad 8H, 1.50 d 6H.

6-((4-Aminomethyl)-benzyl-aminomethyl)-3-amino-2-methyl-1,4-benzoxazine trihydrochloride 6-(para-(N-[3-Amino-2-methyl-2H-1,4-benzoxazin-6-yl]-methyl-aminomethyl)-benzyl-aminomethyl)-3-amino-2-methyl-2H-1,4-benzoxazine trihydrochloride (HCl content is not determined)

[1H]-NMR (DMSO): 9.9 broad, 9.5 broad, 7.64 s 4H, 7.48 dd 2H, 7.35 dd 2H, 7.12 d 2H, 5.33 q 2H, 4.19 broad 4H, 4.11 broad 4H, 1.50 d 6H.

6-(para-(N-3-Keto-2-methyl-2H-1,4-benzoxazin-6-yl]-methyl-aminomethyl)-benzyl-aminomethyl)-3-amino-2-methyl-2H-1,4-benzoxazine trihydrochloride 6-((3-aminomethyl-cyclohex-1-yl)-methyl-aminomethyl)-3-amino-2-methyl-2H-1,4-benzoxazine trihydrochloride

[1H]-NMR (DMSO) 9.4 broad, 8.1 broad s, 7.5 d 1H, 7.43 d 1H, 7.12 d 1H, 5.34 q 1H, 4.12 broad 2H, 1.2 to 2.9 m 14 H, 1.51 d 3H.

6-(3-(N-[3-Amino-2-methyl-2H-1,4-benzoxazin-6yl]-methyl-aminomethyl)-cyclohex-1-ylmethyl-aminomethyl)-3-amino-2-methyl-1,4-benzoxazine trihydrochloride (HCl content is not determined)

6-((omega-Aminobutyl-aminomethyl)-3-amino-2-methyl-2H-1,4-benzoxazine trihydrochloride 6-((omega-aminopentyl-aminomethyl)-3-amino-2-methyl-2H-1,4-benzoxazine trihydrochloride Yield 84%

[1H]-NMR (DMSO): 13.2 broad, 10.1 broad, 9.0 broad, 7.48 d 1H, 7.37 d 1H, 7.13 d 1H, 5.34 q 1H, 4.10 broad 2H, 2.7 to 2.9 m 4H, 0.85 to 1.78 m 6H, 1.50 d 3H.

6-((omega-Aminohexyl-aminomethyl)-3-amino-2-methyl-2H-1,4-benzoxazine trihydrochloride 6-((3-[4-nitrobenzyl]-aminomethyl)-benzylaminomethyl)-3-amino-2-methyl-2H-1,4-benzoxazine trihydrochloride 1H]-NMR (DMSO), 9.9 broad, 8.28 d 2H, 7.92 d 2H, 7.77 s 1H, 7.65d 2H, 7.5 m 2H, 7.39 m 1H, 7.11 d 1H, 5.34 q 1H, 4.35 broad s 2H, 4.21 s 2H, 4.16 s 4H, 1.51 d 3H.

6-((3-[2-Methylbenzyl]-aminomethyl)-benzylaminomethyl)-3-amino-2-methyl-2H-1,4-benzoxazine trihydrochloride 6-((3-[2,4-dichlorobenzyl]-aminomethyl)-benzylaminomethyl)-3-amino-2-methyl-2H-1,4-benzoxazine trihydrochloride 6-((3-[3-chlorobenzyl]-aminomethyl)-benzylaminomethyl)-3-amino-2-methyl-2H-1,4-benzoxazine trihydrochloride 6-((3-[3,4-dichlorobenzyl]-aminomethyl)-benzylaminomethyl)-3-amino-2-methyl-2H-1,4-benzoxazine trihydrochloride 6-((3-benzylaminomethyl)-benzylaminomethyl)-3-amino-2-methyl-2H-1,4-benzoxazine trihydrochloride 6-(3-Aminopropyl-aminomethyl)-3-amino-2-methyl-2H-1,4-benzoxazine trihydrochloride 6-(3-[N-methylamino]-propyl-aminomethyl)-3-amino-2-methyl-2H-1,4-benzoxazine trihydrochloride

[1H]-NMR (DMSO): 9–10 m broad NH, 7.49 d 1H, 7.40 dd 1H, 7.12 d 1H, 5.39 q 1H, 4.11 d 2H, 2.5 s 3H, 3.05 m 4H, 2.12 m 2H, 1.51d 3H.

6-{(3-[N-3-Chlorobenzyl]-aminopropyl}-aminomethyl)-3-amino-2-methyl-2H-1,4-benzoxazine trihydrochloride

[1H]-NMR (DMSO): 9.6 m broad, 7.74 s 1H, 7.57 dd 1H, 7.49 d 3H, 7.39 d 1H, 7.12 d 1H, 5.35 q 1H, 4.15 s 2H, 4.10 s broad 2H, 3.05 m 4H, 2.15 m 2H, 1,49 d 3H.

6-(4-{[N-3-Chlorobenzyl]-amino-n-butyl}-aminomethyl)-3-amino-2-methyl-2H-1,4-benzoxazine trihydrochloride [1H]-NMR (DMSO): 9.5 m broad, 7.75 s 1H, 7.57 dd 1H, 7.49 m 3H, 7.39 dd 1H, 7.12 d 1H, 5.37 q 1H, 4.10 d broad 4H, 2.9 m 4H, 1.74 in 4H, 1,49 d 3H.

6-(4-{[N-2-Thienylmethyl]-amino-n-butyl}-aminomethyl)-3-amino-2-methyl-2H-1,4-benzoxazine trihydrochloride

[1H]-NMR (DMSO) 9.5 m broad, 7.63 d 1H, 7.47 s 1H, 7.38 dd 2H, 7.1 m 2H, 5.34 q 1H, 4.35 s broad 2H, 4.09 s broad 2H, 2.9 m 4H, 1.75 m 4H, 1.50 d 3H.

6-(5-{[N-3-Chlorobenzyl]-amino-n-pentyl}-aminomethyl)-3-amino-2-methyl-2H-1,4-benzoxazine trihydrochloride

[1H]-NMR (DMSO): 9.5 m broad, 7.74 s 1H, 7.56 dd 1H, 7.47 m 3H, 7.38 dd 1H, 7.11 d 1H, 5.35 q 1H, 4.15 d 2H, 4.09 d 2H, 2.9 m 4H, 1.72 m 4H, 1.51 d 3H, 1,4 m 2H.

6-(6-{[N-3-Chlorobenzyl]-amino-n-hexyl}-aminomethyl)-3-amino-2-methyl-2H-1,4-benzoxazine trihydrochloride 6-(4-{[N-4-Fluorobenzyl]-amino-n-butyl}-aminomethyl)-3-amino-2-methyl-2H-1,4-benzoxazine trihydrochloride

[1H]-NMR (DMSO): 9.5 m broad, 7.67 m 2H, 7.48 s 1H, 7.39 dd 1H, 7.29 dd 2H, 7.12 d 1H, 5.37 q 1H, 4.1 m 4H, 2.9 m 4H, 1.75 m 4H, 1.50 d 3H.

6-(4-{[N-3-Trifluorobenzyl]-amino-n-butyl}-aminomethyl)-3-amino-2-methyl-2H-1,4-benzoxazine trihydrochloride

[1H]-NMR (DMSO): 9.6 m broad, (8.05 s, 7.93 d, 7.8 d, 7.7 dd, 7.47 s, 7.39 d, 7.13 d, in each case 1H), 5.36 q 1H, 4.25 broad 2H, 4.10 broad 2H, 2.9 m 4H, 1.78 m 4H, 1.50 d 3H.

6-(4-{[N-ortho-Hydroxybenzyl]-amino-n-butyl}-aminomethyl)-3-amino-2-methyl-2H-1,4-benzoxazine trihydrochloride 6-(5-{[N-isopropyl]-amino-n-pentyl}-aminomethyl)-3-amino-2-methyl-2H-1,4-benzoxazine trihydrochloride p [1H1]-NMR (DMSO): 9.5 m broad, 9.9 m broad NH, 7.49 d 1H, 7.39 dd 1H, 7.13 d 1H, 5.37 q 1H, 4.10 s 2H, 3.2 hept 1H, 2.85 m 4H, 1.7 m 4H, 1.4 m 2H, 1.51 d 3H, 1.26 d 6H.

6-(4-{[-Isopropyl]-amino-n-butyl}-aminomethyl)-3-amino-2-methyl-2H-1,4-benzoxazine trihydrochloride

[1H]-NMR (DMSO): 9.5 m broad, 9 m broad NH, 7.48 d 1H, 7.39 dd 1H, 7.12 d 1H, 5.35 q 1H, 4.11 s 2H, 3.25 hept 1H, 2.9 m 4H, 1.75 m 4H, 1.5 d 3H, 1.27 d 6H.

6-(3-{[N-Isopropyl]-amino-n-propyl}-aminomethyl)-3-amino-2-methyl-2H-1,4-benzoxazine trihydrochloride
[1H]-NMR (DMSO): 9.5 m broad, 9.1 m broad NH, 7.49 d 1H, 7.4 dd 1H, 7.12 d 1H, 5.35 q 1H, 4.11 s 2H, 3.3 hept 1H, 3.0 m 4H, 2.1 m 2H, 1.5 d 3H, 1.27 d 6H.

6-(4-{[N-Cyclopropyl]-amino-n-butyl}-aminomethyl)-3-amino-2-methyl-2H-1,4-benzoxazine trihydrochloride.

6-(4-{[N-cyclopentyl]-amino-n-butyl}-aminomethyl)-3-amino-2-methyl-2H-1,4-benzoxazine trihydrochloride [1h3-NMR (DMSO): 99.5 m broad, 9.1 m broad NH, 7.48 d 1H, 7.39 dd 1H, 7.12 d 1H, 5.37 q 1H, 4.09 s 2H, 2.9 m 4H, 1.95 m 2H, 1.7 m 8H, 1.50 d 3H, 1.52 m 1H.

6-(4-{[N-(Cyclohexyl)-methyl]-amino-n-butyl}-aminomethyl)-3-amino-2-methyl-2H-1,4-benzoxazine trihydrochloride

[1H]-NMR (DMSO): 9.–10 m broad NH, 749 d 1H, 7.39 dd 1H, 7.12 d 1H, 5.37 q 1H, 4.10 d 2H, 2.91 m 4H, 2.74 m 2H, 1.85 to 1.6 m 10H, 1.50 d 3H, 1.3 to 0.85 m 5H.

6-(4-{[N-(cyclopropyl)-methyl]-amino-n-butyl}-aminomethyl)-3-amino-2-methyl-2H-1,4-benzoxazine trihydrochloride 6-(4-{[N-2,2,2-trifluoroethyl]-amino-n-butyl}-aminomethyl)-3-amino-2-methyl-2H-1,4-benzoxazine trihydrochloride

[1H]-NMR (DMSO): 9.5 m broad, 7.49 d 1H, 7.39 dd 1H, 7.11 d 1H, 5.37 q 1H, 4.1 s 2H, 3.99 m 2h (CH$_2$CF$_3$), 3.02 m 2H, 2.92 m 2H, 1.75 m 4H, 1.50 d 3H.

6-(4-{[N-4,4,4-trifluorobutyl]-amino-n-butyl}-aminomethyl)-3-amino-2-methyl-2H-1,4-benzoxazine trihydrochloride 6-{[4-Amino-n-butyl]-amino}-6,7,8,9-tetrahydro-3-amino-2-methyl-2H-naphth[2,3-b]-1,4-oxazine trihydrochloride 6-{[5-amino-n-pentyl]-amino}-6,7,8,9-tetrahydro-3-amino-2-methyl-2H-naphth[2,3-b]-1,4-oxazine trihydrochloride 6-{[3-aminomethyl]-benzylamino}-6,7,8,9-tetrahydro-3-amino-2-methyl-2H-naphth[2,3-b]-1,4-oxazine trihydrochloride

[1H-NMR (DMSO): 9.5 to 8.5 m broad, 7.9 s 1H, 7.8 d 1H, 7.64 d 1H, 7.53 m 2H, 7.0 s 1H, 5.41 q 1H, 4.5 m 1H, 4.3 s 2H, 4.1 s 2H, 2.9 m 2H, 2.3 m 1H, 2.1 m 2H, 1.8 m 1H, 1.55 d 3H.

6-{[4-(N-Isopropylamino)-n-butyl]-amino}-6,7,8,9-tetrahydro-3-amino-2-methyl-2H-naphth[2,3-b]-1,4-oxazine trihydrochloride 6-{[5-(N-isopropylamino)-n-pentyl]-amino}-6,7,8,9-tetrahydro-3-amino-2-methyl-2H-naphth[2,3-b]-1,4-oxazine trihydrochloride 1H]-NMR(MeOH): 7.34 s 1H, 6.85 s 1H, 5.13 q 1H, 4.4 m 1H, 3.29 m 1H, 3.05 dtr 2H, 2.92 m 2H, 2.8 m 2H, 2.15 m 1H, 2.0 m 1H, 1.8 m 2H, 1.7 m 2H, 1.6 m 2H, 1.47 d 3H, 1.24 d 6H.

6-{[4-amino-n-butyl]-amino}-6,7-trimethylen-3-amino-2-methyl-2H-1,4-benzoxazine trihydrochloride 6-{[5-amino-n-pentyl]-amino}-6,7-trimethylen-3-amino-2-methyl-2H-1,4-benzoxazine trihydrochloride 6-{[4-(n-isopropylamino)-n-butyl]-amino}-6,7-trimethylen-3-amino-2-methyl-2H-1,4-benzoxazine trihydrochloride

[1H]-NMR(MeOH): 7.51 s 1H, 7.0 s 1H, 5.13 q 1H, 4.7 m 1H, 3.3 3 m 1H, 3.1 m 2H, 3.0 m 2H, 2.9 m 2H, 2.5 m 1H, 2.2 m 1H, 1.8 m 2H, 1.7 m 2H, 1,49 d 3H, 1.27 d 6H.

6-{[5-(n-isopropylamino)-n-pentyl]-amino}-6,7-trimethylen-3-amino-2-methyl-2H-1,4-benzoxazine trihydrochloride 6-{[3-aminomethyl]-benzylamino}-6,7-trimethylen-3-amino-2-methyl-2H-1,4-benzoxazine trihydrochloride The following are obtained according to commonly used methods:

6-(5-{[N-propyl]-amino-n-pentyl}-aminomethyl)-3-amino-2-methyl-2H-1,4-benzoxazine succinate [stoichiometry 1–1.5 times]

119.4° C.

6-(5-{[N-Isopropyl]-amino-n-pentyl}-aminomethyl)-3-amino-2-methyl-2H-1,4-benzoxazine trispropionate Flash point: 134.9° C.

6-(5-{[N-Isopropyl]-amino-n-pentyl}-aminomethyl)-3-amino-2-methyl-2H-1,4benzoxazine oxalate [stoichiometry 1–1.5 times]

Flash point: 215.2° C.

What is claimed is:

1. A compound of Formula I, or a tautomeric or isomeric form or a salt of a compound of Formula I,

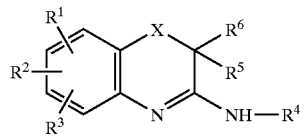

(I)

wherein

X is O, $R^1$ is —(CHR$^9$)$_n$—NR$^7$—A—NR$^8$—Y, $R^2$ is hydrogen, or $R^1$ and $R^2$ together with two adjacent carbon atoms form a 5-, 6-, 7- or 8-membered ring, which is monocyclic or bicyclic, saturated or unsaturated and in which 1 or 2 CH$_2$ groups can be replaced by oxygen or carbonyl, and which is substituted with (CHR$^9$)$_r$—NR$^7$—A—NR$^8$—Y, and is optionally substituted with C$_{1-4}$ alkyl, $R^3$ is hydrogen, halogen, NO$_2$, cyano, CF$_3$, —OCF$_3$, —S—R$^9$, —O—R$^9$, C$_{3-7}$ cycloalkyl, —NR$^9$—C(=NR$^{10}$)—R$^{11}$, —NH—CS—NR$^{12}$R$^{13}$, —NH—CO—NR$^{12}$R$^{13}$, —CO—R$^{14}$, NR$^{15}$R$^{16}$, C$_{6-10}$ aryl, which optionally is substituted with halogen, cyano, C$_{1-4}$ alkyl, —S—R$^9$, or —O—R$^9$, or is thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-C$_{1-6}$ alkyl-3-amino-1,4-benzoxazine, or is 2-C$_{1-6}$-alkyl-3-keto-1,4-benzoxazine, or a C$_{1-6}$ alkyl, which is optionally substituted with halogen, —OR$^9$, —SR$^9$, —NR$^{12}$R$^{13}$, =NR$^{12}$, =NOC$_{1-6}$ alkyl, =N—NHaryl, phenyl, C$_{3-7}$ cycloalkyl or with thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, or is a C$_{2-6}$ alkinyl, which is optionally substituted with halogen, CONH$_2$, C≡N or phenyl, $R^4$ is hydrogen or acyl, $R^5$ and $R^6$, independently of one another, are hydrogen, C$_{3-7}$ cycloalkyl, phenyl, C$_{1-6}$ alkyl, C$_{2-6}$ alkenyl or C$_{2-6}$ alkynyl radicals, which are optionally and independently of one another substituted with halogen, OH, O—C$_{1-6}$ alkyl, SH, S—C$_{1-6}$ alkyl, NR$^{15}$R$^{16}$, thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, phenyl or C$_{3-7}$ cycloalkyl, $R^7$ is hydrogen, C$_{1-6}$ alkyl, which is optionally substituted with phenyl, COOC$_{1-6}$ alkyl or CO—C$_{1-6}$ alkyl, $R^8$ is hydrogen, C$_{1-6}$ alkyl, which is optionally substituted with phenyl, COOC$_{1-6}$ alkyl or COC$_{1-6}$ alkyl, A is a straight-chain or branched C$_{1-6}$ alkylene, or —(CH$_2$)$_p$—Q—(CH$_2$)$_q$—, Y is hydrogen or —(CH$_2$)$_p$—U, Q is C$_{3-7}$ cycloalkyl, indanyl, 5-, 6- or 7-membered saturated heterocycloalkyl with 1–2 N, O or S atoms, C$_6$–C$_{10}$ aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-C$_{1-6}$ alkyl-3-amino-1,4-benzoxazine, or 2-C$_{1-6}$-alkyl-3-keto-1,4-benzoxazine, U is hydrogen, C$_{1-6}$ alkyl optionally substituted with halogen, C$_{3-7}$ cycloalkyl, indanyl, C$_{7-10}$ bicycloalkyl, C$_{6-10}$ aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-C$_{1-6}$ alkyl-3-amino-1,4-benzoxazine, or 2-C$_{1-6}$-alkyl-3-keto-1,4-benzoxazine, wherein the aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-C$_{1-6}$ alkyl-3-amino-1,4-benzoxazine, or 2-C$_{1-6}$ -alkyl-3-keto-1,4-benzoxazine, is optionally substituted with halogen, C$_{1-4}$ alkyl, C$_{1-4}$ alkoxy, CF$_3$, NO$_2$, N$_2$, N(C$_{1-4}$ alkyl)$_2$, cyano, CONH$_2$, —O—CH$_2$—O—, —O—(CH$_2$)$_2$—O—, SO$_2$NH$_2$, OH, phenoxy or COOC$_{1-4}$ alkyl, $R^8$ and Y together with the nitrogen atom optionally form a 5- to 7-membered saturated heterocycle, which optionally has another oxygen, nitrogen or sulfur atom and is optionally substituted with C$_{1-4}$ alkyl, phenyl, benzyl or benzoyl or form an unsaturated 5-membered heterocycle, which optionally has 1–3 N atoms and is optionally substituted with phenyl, C$_{1-4}$ alkyl or halogen, $R^7$ and A together with the nitrogen atom optionally form a 5- to 7-membered saturated heterocycle, which optionally has another oxygen, nitrogen or sulfur atom or form an unsaturated 5-membered heterocycle, which optionally has 1–3 N atoms, m is 0, 1 or 2, n and r is 0, 1 to 6, p and q is 0 to 6, $R^9$ and $R^{10}$ is hydrogen or C$_{1-6}$ alkyl, $R^{11}$ is C$_{1-6}$ alkyl, —NH$_2$, —NH—CH$_3$, —NH—CN, C$_{6-10}$ aryl optionally substituted with halogen, C$_{1-4}$ alkyl or CF$_3$, or an unsubstituted or substituted with halogen, C$_{1-4}$ alkyl or CF$_3$ group selected from the group consisting of thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-C$_{1-6}$ alkyl-3-amino-1,4-benzoxazine, and 2-C$_{1-6}$-alkyl-3-keto-1,4-benzoxazine, $R^{12}$ and $R^{13}$ are hydrogen, C$_{1-6}$, alkyl, phenyl optionally substituted with halogen or C$_{1-4}$ alkyl, benzyl optionally substituted with halogen or C$_{1-4}$ alkyl, or C$_{3-7}$ cycloalkyl, $R^{14}$ is hydrogen, hydroxy, C$_{1-6}$ alkoxy, phenyl, C$_{1-6}$ alkyl optionally substituted with CO$_2$H, CO$_2$C$_{1-6}$ alkyl, hydroxy, C$_{1-4}$ alkoxy, halogen, NR$^{15}$R$^{16}$, CONR$^{12}$R$^{13}$, phenyl, or C$_{2-6}$ alkenyl optionally substituted with phenyl, cyano, CONR$^{12}$R$^{13}$ or CO$_2$C$_{1-4}$ alkyl, $R^{15}$ and $R^{16}$ are hydrogen, $C_{1-6}$ alkyl, phenyl or benzyl, and $R^{15}$ and $R^{16}$ together with the nitrogen atom optionally form a saturated 5-, 6-, or 7-membered ring, which optionally has another nitrogen, oxygen or sulfur atom and is optionally substituted with $C_{1-4}$ alkyl, phenyl, benzyl or benzoyl.

2. A compound according to claim 1, wherein $R^1$ and $R^2$ together with two adjacent carbon atoms form the 3- to 8-membered ring that is substituted with—$(CHR^9)_r$—$NR^7$—A—$NR^8Y$.

3. A compound according to claim 2, wherein r=0.

4. A compound according to claim 1, wherein A is a straight-chain or branched $C_{1-6}$ alkylene or —$(CH_2)_p$—Q—$(CH_2)_q$—, wherein p and q are each independently 1–4.

5. A compound according to claim 1, wherein U is hydrogen, alkyl that is optionally substituted with halogen, $C_{3-7}$ cycloalkyl or optionally substituted phenyl.

6. A compound according to claim 1, wherein $R^{11}$ is thienyl.

7. A compound according to claim 1, wherein $R^8$ and Y together or $R^7$ and A together, independently of each other, is selected from the group consisting of imidazole, pyrrole, pyrazole and triazole.

8. A compound according to claim 1, wherein U is hydrogen, $C_{1-6}$ alkyl optionally substituted with halogen, $C_{3-7}$ cycloalkyl, indanyl, $C_{7-10}$ bicycloalkyl, or $C_{6-10}$ aryl.

9. A compound according to claim 1, wherein saturated heterocycle is piperidine, pyrrolidine, morpholine, thiomorpholine, hexahydroazepine, piperazine, N-methyl-piperazine, 2,6-dimethylmorpholine, phenylpiperazine or 4(4-fluorobenzoyl)-piperidine.

10. A compound according to claim 1, wherein $R^8$ and Y together or $R^7$ and A together, independently of each other, form a 5- to 7-membered saturated heterocycle.

11. A compound according to claim 1, wherein $R^8$ and Y together or $R^7$ and A together, independently of each other, form a 5- to 7-membered saturated heterocycle selected from the group consisting of piperidine, pyrrolidine, morpholine, thiomorpholine, hexahydroazepine, piperazine, N-methyl-piperazine, 2,6-dimethylmorpholine, phenylpiperazine, and 4-(4-fluorobenzoyl)-piperidine.

12. A compound according to claim 1, which is 6-((3-aminomethyl)-benzyl-aminomethyl)-3-amino-2-methyl-2H-1,4-benzoxazine trihydrochloride, 6-(meta-(N-[3-keto-2-methyl-2H-1,4-benzoxazin-6-yl]-methyl-aminomethyl-benzyl-aminomethyl)-3-amino-2-methyl-2H-1,4-benzoxazine trihydrochloride, 6-(meta-(N-[3-amino-2-methyl-2H-1,4-benzoxazin-6-yl]-methyl-aminomethyl-benzyl-aminomethyl )-3-amino-2-methyl-2H-1,4-benzoxazine trihydrochloride, 6-((4-aminomethyl)-benzyl-aminomethyl)-3-amino-2-methyl-2H-1,4-benzoxazine trihydrochloride, 6-(para-(N-[3-amino-2-methyl-2H-1,4-benzoxazin-6-yl]-methyl-aminomethyl)-benzyl-aminomethyl)-3-amino-2-methyl-2H-1,4-benzoxazine trihydrochloride, 6(para-(N-[3-keto-2-methyl-2H-1,4-benzoxazin-6-yl]-methyl-aminomethyl)-benzyl-aminomethyl)-3-amino-2-methyl-2H-1,4-benzoxazine trihydrochloride, 6-((3-aminomethyl-cyclohex-1-yl)-methyl-aminomethyl)-3-amino-2-methyl-2H-1,4-benzoxazine trihydrochloride, 6-(3-(N-[3-amino-2-methyl-2H-1,4-benzoxazin-6-yl]-methyl-aminomethyl)-cyclohex-1-ylmethyl-aminomethyl)-3-amino-2-methyl-2H-1,4-benzoxazine trihydrochloride, 6-((omega-aminobutyl-aminomethyl)-3-amino-2-methyl-2H-1,4-benzoxazine trihydrochloride, 6-((omega-aminopentyl-aminomethyl)-3-amino-2-methyl-2H-1,4-benzoxazine trihydrochloride, 6-((omega-aminohexyl-aminomethyl)-3-amino-2-methyl-2H-1,4-benzoxazine trihydrochloride, 6-((3-[4-nitrobenzyl]-aminomethyl)-benzylaminomethyl)-3-amino-2-methyl-2H-1,4-benzoxazine trihydrochloride, 6-((3-[2-methylbenzyl]-aminomethyl)-benzylaminomethyl)-3-amino-2-methyl-2H-1,4-benzoxazine trihydrochloride, 6-((3-[2,4-dichlorobenzyl]-aminomethyl)-benzylaminomethyl)-3-amino-2-methyl-2H-1,4-benzoxazine trihydrochloride, 6-((3-[chlorobenzyl]-aminomethyl)-benzylaminomethyl)-3-amino-2-methyl-2H-1,4-benzoxazine trihydrochloride, 6-((3-[3,4-dichlorobenzyl]-aminomethyl)-benzylaminomethyl)-3-amino-2-methyl-2H -1,4-benzoxazine trihydrochloride, or 6-((3-benzylaminomethyl)-benzylaminomethyl)-3-amino-2-methyl-2H-1,4-benzoxazine trihydrochloride.

13. A process for preparing a compound of claim 1, comprising reacting a compound of formula IIa or IIb or a salt thereof

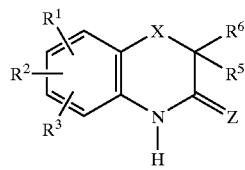

IIa

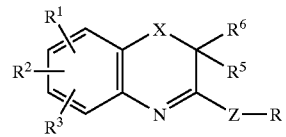

IIb wherein $R^1$, $R^2$, $R^3$, $R^5$, $R^6$ and X are as defined in claim 1, Z is oxygen or sulfur and R is a $C_{1-6}$ alkyl, with $NH_2R^4$, wherein $R^4$ is as defined in claim 1.

14. A compound of formula IIa or IIb

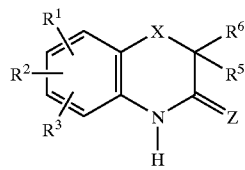

IIa

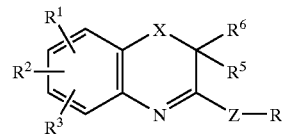

IIb wherein $R^1$ is —$(CHR^9)_n$—$NR^7$—A—$NR^8$—B, $R^2$, $R^3$, $R^4$ and $R^4$ are hydrogen, $R^6$ is methyl, X is oxygen, R is a $C_{1-6}$ alkyl, Z is oxygen or sulfur, $R^7$ is hydrogen, $C_{1-6}$ alkyl, which is optionally substituted with phenyl, $COOC_{1-6}$ alkyl or CO—$C_{1-6}$ alkyl, $R^8$ is hydrogen, $C_{1-6}$ alkyl, which is optionally substituted with phenyl, $COOC_{1-6}$ alkyl or $COC_{1-6}$ alkyl, A is a straight-chain or branched $C_{1-6}$ alkylene, or $—(CH_2)_p—O—(CH_2)_q—$, B is hydrogen or $—(CH_2)_p—U$, Q is $C_{3-7}$ cycloalkyl, indanyl, 5-, 6- or 7-membered saturated heterocycloalkyl with 1–2 N, O or S atoms, $C_6$–$C_{10}$ aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-$C_{1-6}$ alkyl-3-amino-1,4-benzoxazine, or 2-$C_{1-6}$-alkyl-3-keto-1,4-benzoxazine, U is hydrogen, $C_{1-6}$ alkyl optionally substituted with halogen, $C_{3-7}$ cycloalkyl, indanyl, $C_{7-10}$ bicycloalkyl, $C_{6-10}$ aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-$C_{1-6}$ alkyl-3-amino-1,4-benzoxazine, or 2-$C_{1-6}$-alkyl-3-keto-1,4-benzoxazine, wherein the aryl or thienyl, imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline, 2-$C_{1-6}$ alkyl-3-amino-1,4-benzoxazine, or 2-$C_{1-6}$-alkyl-3-keto-1,4-benzoxazine, is optionally substituted with halogen, $C_{1-4}$ alkyl, $C_{1-4}$ alkoxy, $CF_3$, $NO_2$, $NH_2$, $N(C_{1-4}$ alkyl$)_2$, cyano, $CONH_2$, $—O—CH_2—O—$, $—O—(CH_2)_2—O—$, $SO_2NH_2$, OH, phenoxy or $COOC_{1-4}$ alkyl, $R^8$ and B together with the nitrogen atom optionally form a 5- to 7-membered saturated heterocycle, which optionally has another oxygen, nitrogen or sulfur atom and is optionally substituted with $C_{1-4}$ alkyl, phenyl, benzyl or benzoyl or form an unsaturated 5-membered heterocycle, which optionally has 1–3 N atoms and is optionally substituted with phenyl, $C_{1-4}$ alkyl or halogen, $R^7$ and A together with the nitrogen atom optionally form a 5- to 7-membered saturated heterocycle, which optionally has another oxygen, nitrogen or sulfur atom or form an unsaturated 5-membered heterocycle, which optionally has 1–3 N atoms, n is 0, 1 to 6, p and q is 0 to 6, and $R^9$ is hydrogen or $C_{1-6}$ alkyl.

15. A pharmaceutical composition comprising a compound according to claim 1 and one or more pharmaceutically acceptable auxiliaries.

16. A method of treating a disease that is triggered by NOS comprising administering to a patient in need thereof a pharmaceutical composition according to claim 15.

17. A method of treating a neurodegenerative disease comprising administering to a patient in need thereof a pharmaceutical composition according to claim 15.

* * * * *